Figure 1:
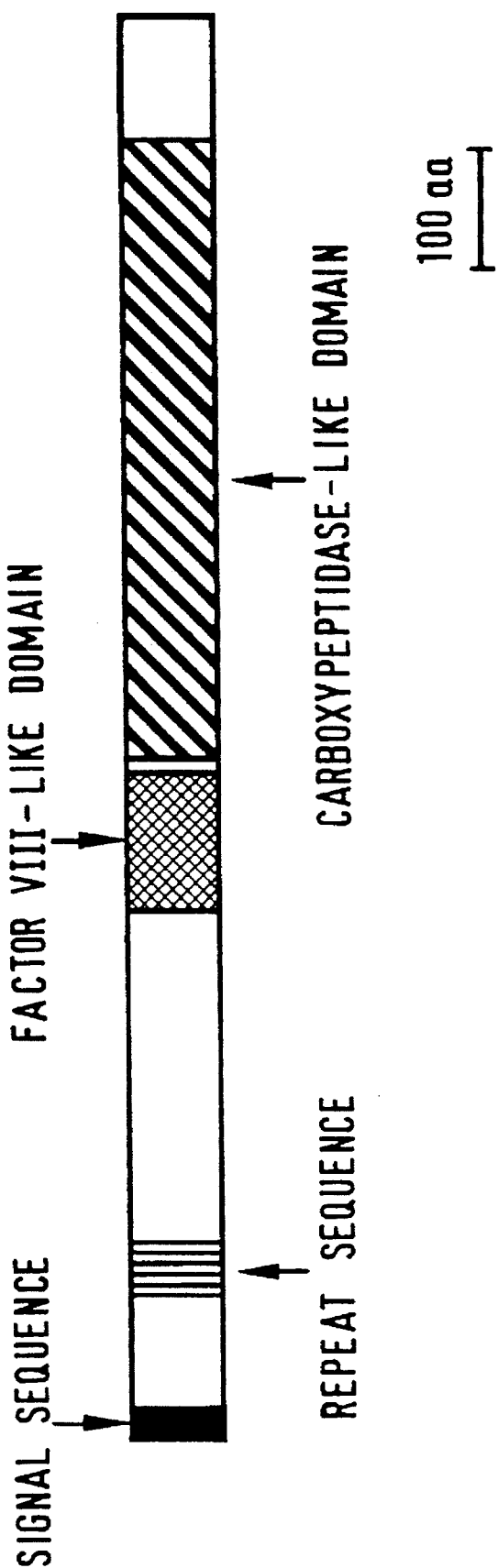

United States Patent [19]

Kawai et al.

[11] Patent Number: 5,460,951
[45] Date of Patent: Oct. 24, 1995

[54] BONE-RELATED CARBOXYPEPTIDASE-LIKE PROTEIN AND PROCESS FOR ITS PRODUCTION

[75] Inventors: Shinji Kawai, Fujimi; Sunao Takeshita, Tokorozawa; Makoto Okazaki, Kawagoe; Egon Amann, Tokyo, all of Japan

[73] Assignee: Hoechst Japan Limited, Tokyo, Japan

[21] Appl. No.: 111,939

[22] Filed: Aug. 26, 1993

[30] Foreign Application Priority Data

Aug. 28, 1992 [JP] Japan .................................. 4-230029
Dec. 3, 1992 [JP] Japan .................................. 4-324033

[51] Int. Cl.$^6$ ............................ C12P 21/00; C12P 21/02; C12N 15/12
[52] U.S. Cl. ...................... 435/69.1; 435/172.3; 435/212; 536/23.2
[58] Field of Search ............................... 435/69.1, 172.3, 435/212; 536/23.1, 23.2, 23.5

OTHER PUBLICATIONS

USB Molecular Biology Reagents/Protocols 1992, published by United States Biochemical (1991), pp. 315–319.
"Basic carboxypeptidases: regulators of peptide hormone activity ", Randal A. Skidgel, Trends Pharmacol. Sci., 9:299–304 (1988).
"Inhibition of Bone Resorption In Vitro by Human Enkephalinase (EC 3.424.11), a Neutral Metalloendopeptidase", Ibbotson et al., Journal of Bone and Mineral Research, 7(3):273–279 (1992).
S. Howell, et al., Membrane Peptidases on Human Osteoblast–Like Cells in Culture: Hydrolysis of Calcitonin and Hormonal Regulation of Endopeptidase–24 .11; Biochemical Journal, vol. 290, part 1: 159–164 (Feb. 15, 1993).
EPO Search Report
Critical Synergy: The Biotechnology Industry and Intellectual Property Protection Presentation of the Intellectual Property Committee of the Biotechnology Industry Organization at the Oct. 17, 1994 Hearing of the U.S. Patent & Trademark Office, San Diego, Cal. published by the Biotechnology Industry Organization (1994), p. 100.
Suggs et al, Proc. Natl Acad. Sci. USA 78: 6613 (1981).
Marcus—Sekura, Anal. Biochem. 172: 289 (1988).
Sakai et al, Genomics 5: 309 (1989).
Lewin, Gene Expression, vol. 2, Eucaryotic Chromosomes, 1974, John Wiley & Sons, New York, N.Y. pp. 160–169.

Primary Examiner—James Martinell
Attorney, Agent, or Firm—Finnegan, Henderson, Farabow, Garrett & Dunner

[57] ABSTRACT

A bone-related carboxypeptidase-like protein named OSF-5 which is obtained from bone tissue of a mammal including mouse or human, and a process for its production. This protein is a novel naturally occurring mammal protein which belongs to a group of carboxypeptidase molecules.

OSF-5 acts as an adhesion molecule or a growth factor which takes part in the process of osteogenesis at the site of bone induction. OSF-5 can be used as an agent for treating bone metabolic diseases, and its high organ specificity for bones enables its use as a diagnostic reagent for bone metabolic diseases.

5 Claims, 3 Drawing Sheets

1 THYMUS

2 SPLEEN

3 BRAIN

4 KIDNEY

5 LIVER

6 LUNG

7 TESTIS

8 HEART

9 OSTEOBLAST-ENRICHED CELL FROM MOUSE CALVARIA

10 MC3T3-E1 CELLS FROM 3 DAYS CULTURE

11 MC3T3-E1 CELLS FROM 12 DAYS CULTURE

12 MC3T3-E1 CELLS FROM 60 DAYS CULTURE

13 NIH3T3 CELLS

BONE-RELATED CARBOXYPEPTIDASE-LIKE PROTEIN AND PROCESS FOR ITS PRODUCTION

This invention provides a novel bone-related protein. Named OSF-5, this protein belongs to a group of carboxypeptidase molecules. The OSF-5 can be obtained from bone tissue of a mammal including mouse or human. The present invention also provides a process for producing the OSF-5 by recombinant DNA technology using cultured cells such as animal cells.

Bone metabolic diseases include osteoporosis, Paget's disease, osteomalacia, hyperostosis, and osteopetrosis. Osteoporosis, in particular, has a high incidence enough to affect about more than a half of postmenopausal women and elderly people, and effective methods for its diagnosis and treatment have been strongly desired.

Bone metabolic diseases involve some disorder of bone metabolism at the cellular level in bone tissue. The discovery, isolation and identification of factors associated specifically with bone metabolism are very effective for elucidating this disorder.

A cell line of osteoblasts, which play a major role in osteogenesis, was used in the present invention to identify a proteinaceous factor produced specifically by this cell line. Therefore, the present invention refers to a novel protein named OSF-5 which is substantially bone-specific, and which has a high homology with various known carboxypeptidases in terms of amino acid sequence.

OSF-5 can also be produced from the DNA sequence described in the present specification by an ordinary genetic engineering technique known in the art. Furthermore, the OSF-5 or its fragment can be produced from the amino acid sequence described in the specification by a chemical peptide synthesis method.

Moreover, that fragment of the DNA sequence of the OSF-5 described in the present invention which has a high specificity particularly for other carboxypeptidase can be synthesized with a length of 15 to 50 bases by an ordinary chemical oligonucleotide synthesis method. That fragmentary sequence can be used as a DNA probe for finding and identifying bone-derived cells. This identification of bone-derived cells is useful particularly for grasping the origin of metastatic or recurrent carcinoma, thus leading to an appropriate therapy for recurrent cancer. Of the partial peptides of the OSF-5, the peptide in the epitope portion that can be recognized by antibodies is usable for preparing a monoclonal antibody specific for OSF-5. The resulting monoclonal antibody is of marked value for identifying bone-derived cells by an immunological cell tissue staining method.

The following is known about the proteins in a group of carboxypeptidases where the OSF-5 belongs.

Remarkable progress in the study of physiologically active peptides has made the importance of carboxypeptidases clearer. Carboxypeptidases are roughly classified, according to their active center, into metallo carboxypeptidases (E.C.3.4.17), serine carboxypeptidases (E.C.3.4.16), and cysteine carboxypeptidases (E.C.3.4.18). These carboxypeptidases release amino acids specific for them from the C-terminus of a peptide or protein. The metallo carboxypeptidases include basic carboxypeptidases closely related to peptide hormones. Typical of them are carboxypeptidases B, N, H (E) and M. Carboxypeptidase B was discovered as an enzyme to release arginine from protamine. It is widely present as a precursor in the mammalian pancreas, is activated in the digestive tract by the action of trypsin, and plays a role in digestion in cooperation with other digestive enzymes. Carboxypeptidase N (kininase I) is detected in the plasma of animals, and deactivates bradykinin and anaphylatoxin, thus taking part in the homeostasis of kinins. Carboxypeptidase H (enkephalin convertase) was identified as a carboxypeptidase B-like enzyme responsible for the biosynthesis of enkephalins. This enzyme is involved in the processing of peptide hormone precursors, and is localized in secretory granules. Carboxypeptidase M is a cell membrane-bound enzyme capable of controlling the receptor specificity of peptide hormones on the cell surface. Thus, the functions of carboxypeptidases are classified into at least three, (1) to generate active peptides from inactive peptide precursors, (2) to deactivate active peptides, and (3) to change the receptor specificity of peptides (Skidgel, (1988), Trends Pharmacol. Sci. vol. 9, pp. 299–304).

Growth factors and local factors, such as parathyroid hormone, interleukin-1, calcitonin, transforming growth factor-$\beta$ (TGF-$\beta$), bone morphogenetic protein (BMP), insulin-like growth factor (IGF) or fibroblast growth factor (FGF), take part in the process of bone remodeling. Normal bone remodeling is maintained when the biological activity of these factors is strictly controlled. Much is unknown about the mechanisms of this control, but one of the possible mechanisms is by local proteases. Many proteases are present in vivo, of which carboxypeptidases can be noticed for such a mechanism. Namely, carboxypeptidases localized in bone tissue may control the biological activity of the peptide factors involved in bone metabolism. Recently, enkephalinase, a neutral metalloendopeptidase, has been shown to inhibit bone resorption in vitro (Ibbotson et al. (1992), J. Bone Miner. Res., vol. 7, pp. 273–279). Thus, light is gradually being shed on the protease-catalyzed control of bone metabolism.

During bone remodeling, the osteoid is digested by collagenase and plasminogen activator (an enzyme activating collagenase) which may be synthesized mainly in osteoblasts. As a result, the underlying calcified matrix is exposed, and osteoclasts are directed there for resorption of the bone matrix. There is a possibility that carboxypeptidases may be included in the group of proteases synthesized by osteoblasts during the bone remodeling process. The carboxypeptidases may further decompose the degradation products formed by the action of the collagenase and plasminogen activator of osteoblasts. They may also play the role of a scavenger after osteoclasia, i.e. the role of further degrading digested pieces formed by acids or proteases secreted by osteoclasts, thereby creating an environment in which osteoblasts act efficiently at the site of the calcified matrix having undergone osteoclasia. Furthermore, when osteoclasts absorb the calcified matrix, growth factors such as TGF-$\beta$ are secreted normally in the inactive form. These growth factors may be activated by carboxypeptidases. By removing the C-terminal amino acid residue, carboxypeptidases are assumed to supply materials, such as amino acids, necessary for bone formation (protein synthesis) by osteoblasts. However, osteoblast-specific carboxypeptidases have not been known.

Thus, the object of the present invention is to find new carboxypeptidases which are expressed specifically in bone cells, especially osteoblasts. Such bone-derived carboxypeptidases can be generally used for the C-terminal analysis of proteins. Furthermore, because of their bone origin, they control the activity of peptide hormones that act on bone tissue. Besides, they promote the digestion of osteoid tissue as well as the supply of amino acids, and function as a scavenger. Through these actions, they can be expected to treat various bone metabolic diseases.

cDNA of mouse OSF-5 was isolated from the mouse osteoblastic cell line MC3T3-E 1 cDNA library constructed by a combination of PCR (polymerase chain reaction) and the subtraction method, and cloned by the differential screening technique. The resulting clone was named OSF-5, and its DNA sequence determined. Search through the currently available DNA and amino acid sequence data bases showed the DNA sequence of the OSF-5 to be novel.

OSF-5 has a typical signal sequence (25 amino acid residues) generally known to be present in a secretory protein, but contains no typical transmembrane region. OSF-5 has lysine- and proline-rich four-fold repeating units each composed of the 11 amino acid residues, Lys-Pro-Lys-Glu-Lys-Pro-Pro-Lys-Ala-Thr-Lys (SEQ. ID No.: 7), at the 116th to 159th positions from the N-terminus. These 11 amino acid residues show weak homology with prolactin receptor, fibroblast growth factor receptor, gamma aminobutyric acid receptor, serotonin receptor, histone H1, and so on. At the 423rd to 531st positions, there is a domain homologous with the phospholipid binding region of blood coagulation factor VIII. The phospholipid binding region of blood coagulation factor VIII may bind to phospholipids on the cell membrane surface. Thus, said domain directs the OSF-5 itself to the cell membrane surface of particular cells (osteoblasts, chondrocytes, etc.) where the OSF-5 is to function. This action can be used for targeting the OSF-5 at bone tissue as in a drug delivery system. At the 544th to 1027th positions, there is a carboxypeptidase H-homologous domain, which contains almost all regions of carboxypeptidase H. This carboxypeptidase-like domain acts as a controlling element for peptide hormones and cytokines during the process of bone metabolism.

Peptides were synthesized which corresponded to 11 amino acid residues (KPKEKPPKATK) (SEQ ID NO.: 7) at the 116th to 126th positions, and 15 amino acid residues each at the 482nd to 496th positions (GYEEMTFYGNVDKDT) (SEQ. ID. NO.: 8), at the 557th to 571st positions (SYKDMRQLMKAVDEE) (SEQ ID NO.: 9), at the 701st to 715th positions (WAAEEKKWVPYRVPN) (SEQ ID NO.: 10), and at the 872nd to 886th positions (PHESELPREWENNKE) (SEQ ID NO.: 11), each derived from the hydrophilic regions of OSF-5. Each peptide was conjugated with ovalbumin, and used for immunization of rabbits. Anti-OSF-5 peptide antisera obtained were used for immunohistochemical detection of OSF-5 in systemic slices of the mouse neonate. OSF-5 was detected in the osteoblasts and chondrocytes.

Generally, the OSF-5 can be directly extracted from bone tissue or cartilage tissue of a human, bovine, murine or other source by a known biochemical technique.

Moreover, the mouse OSF-5 of the present invention can be used to isolate and identify other mammalian OSF-5 proteins similar in DNA sequence and amino acid sequence. That is, the DNA coding for the OSF-5 can be obtained by constructing a cDNA library or a genomic library from mRNA extracted from vertebrate bone tissue, and using a probe comprising a labeled fragment of the mouse DNA sequence disclosed in the present specification. A full length cDNA clone can be obtained by combining the above-described and other standard techniques on molecular biology.

The present invention further provides polypeptides comprising analogues of OSF-5, i.e. mutants and fused proteins having OSF-5 activity, as well as fragments containing at least 11, preferably 15, particularly the main part of the OSF-5 namely the Factor VIII-like domain and/or the carboxypeptidase-like domain. This invention also provides a process for producing the OSF-5 by recombinant DNA technology.

BRIEF EXPLANATION OF FIGURES AND TABLES

FIG. 1 is a schematic drawing of the structure of mouse OSF-5 precursor protein. OSF-5 is divided into four regions consisting of a signal sequence, four-fold repeating sequence composed of 11 amino acids, blood coagulation factor VIII-like region which may bind to phospholipid on the cell membrane surface, and carboxypeptidase-like region.

Figure 2:
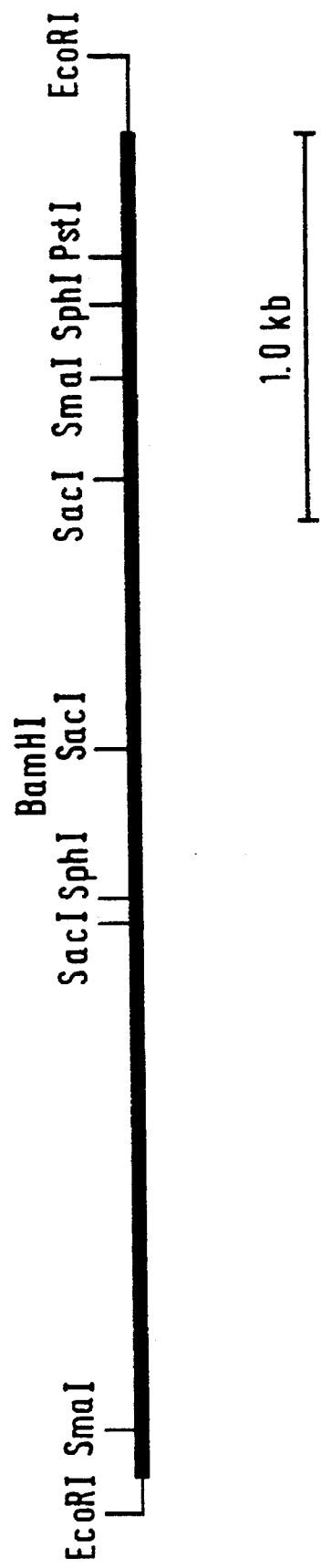

FIG. 2 shows a restriction enzyme map of cDNA coding for mouse OSF-5. The bold letters indicate the region coding for the amino acid of OSF-5. There are no Kpnl, HindIll, Sall and Xbal sites.

Figure 3:
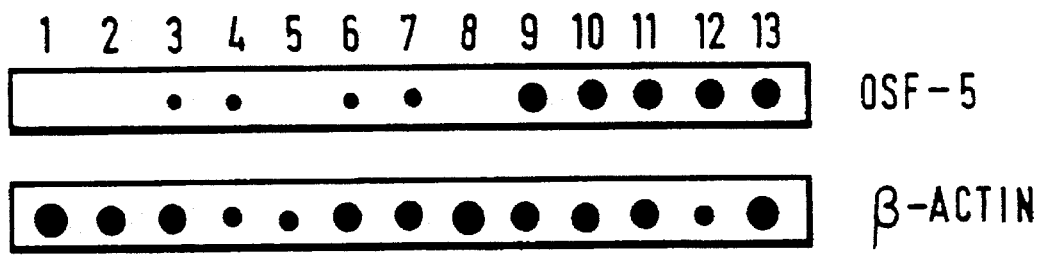

FIG. 3 shows the tissue-specific expression of mouse OSF-5. This was analyzed by purifying RNA from various tissue and cultured cells followed by RNA dot blotting. This diagram shows the results of autoradiography.

Table 1 shows an alignment of the amino acid sequences of mouse OSF-5 and other carboxypeptidase molecules, Common amino acid residues are shown in the form of a consensus.

Table 2 shows a continuation of the alignment of the amino acid sequences of mouse OSF-5 and other carboxypeptidase molecules shown in Table 1. Common amino acid residues are shown in the form of a consensus.

Table 3 shows a continuation of the alignment of the amino acid sequences of mouse OSF-5 and other carboxypeptidase molecules shown in Table 2. Common amino acid residues are shown in the form of a consensus.

Table 4 shows an alignment of the amino acid sequences of mouse OSF-5 and the phospholipid binding region of other blood coagulation factors. Common amino acid residues are shown in the form of a consensus.

This application claims priority from Japanese Application No. 230029/92 and Japanese Application No. 324033/92, the contents of which are incorporated herein by reference.

EXAMPLES

The present invention will be described in more detail by reference to the following Examples:

Example 1

Construction of cDNA library by subtraction and PCR

The construction of a cDNA library specific for the osteoblastic cell line MC3T3-E1 will be hereinafter described, This cDNA library is constructed by a combination of the subtraction method and the PCR with the gene expressed in mouse liver tissue being subtracted. Each cDNA clone has gene fragments with an average length of about 300 bases, and is characterized in that the gene with a low content has been amplified.

Unless otherwise specified, all general recombinant DNA protocols complied with Sambrook et al., "Molecular Cloning Manual" (1989), Cold Spring Harbor Laboratory, Cold Spring Harbor, U.S.A. Total RNAs were extracted from $8 \times 10^7$ MC3T3-E 1 cells and about 1 g of mouse liver tissue by the guanidine method. Poly $A^+$RNAs were purified from the total RNAs by means of the commercially available product "Oligo dT Latex mRNA Purification Kit" (Takara Shuzo). cDNAs were synthesized by a cDNA synthesis kit (Amersham) using 1 μg of each poly A⁺RNA as a template. However, a random primer was used, instead of an oligo dT primer, in an amount of 1.5 times its ordinary amount used, whereby the cDNA chain elongation was restricted to an average length of about 300 bases. After the cDNAs were made double-stranded blunt-ended by use of the above kit, they were joined with T4 DNA ligase (Takara Shuzo) to the below-described two DNA linkers, i.e. ATOS-½ (SEQ. ID NO. 3 and SEQ. ID NO.: 4) for the MC3T3-E1 cDNA, and ATOS-4/5 (SEQ. ID NO.: 5 and SEQ. ID NO.: 6 of the Sequence Table) for the liver cDNA.

ATOS-1/2:
ATOS-1  5'-   CTCTTGCTTGAATTCGGACTA-3'  (SEQ ID NO:3)
ATOS-2  3'-ACACGAGAACGAACTTAAGCCTGAT-5'  (SEQ ID NO:4)

ATOS-4/5:
ATOS-4  5'-   CTCTTGCTTAAGCTTGGACTA-3'  (SEQ ID NO:5)
ATOS-5  3'-ACACGAGAACGAATTCGAACCTGAT-5'  (SEQ ID NO:6)

Then, each reaction product was subjected to DNA amplification by the PCR (polymerase chain reaction) method using ATOS-1 and ATOS-4, respectively, as primers. The amplified DNA concentration was determined with the DNA assay kit "DNA Dipstick" (Invitrogen). The subtraction method was performed using photobiotin (Pirce). Photobiotin (20 ng) was added to 20 μg of the PCR-amplified liver cDNA, and light from a sunlamp 10 cm apart was projected onto the liver cDNA for 10 minutes to label it with biotin. To 3.0 μg of the labeled liver cDNA was added 0.3 μg of unlabeled MC3T3E1 cDNA for hybridization. Then, streptavidin (Takara Shuzo) was reacted, and the reaction mixture was extracted with phenol to remove cDNA common to the liver cDNA from the MC3T3-E1 cDNA. The subtraction method was repeated to remove as much of the common cDNA as possible from the MC3T3-E 1 cDNA. DNA was amplified by PCR using the aforementioned ATOS-1, and the DNA concentration was measured. This cDNA (10 ng) was digested with the restriction enzyme EcoRI, and then ligated with T4 ligase to 1 μg of the phage vector lambda gt10 (lambda gt10/EcoRI cloning kit, Stratagene) which was digested with EcoRI and dephosphorylated at its ends. The resulting recombinant DNA was packaged into lambda phage particles by use of the in vitro packaging kit "Gigapack-gold" (Stratagene). The recombinant phages were infected into E. coil C600 (preserved as HT003 at Japanese Cancer Research Resources Bank, National Institute of Health of Japan), and the organisms were applied to an agar medium along with a soft agar medium to form phage plaques. The efficiency of infection was determined to be 3×10⁶ phage plaques/μg vector DNA.

The resulting cDNA library was subjected to differential screening to select clones with a high specificity for MC3T3-E1. Specifically, 2.25×10⁴ phages were applied to total 10 plates, and the resulting plaques on each plate were transferred to two nylon membrane filters (total 20 filters). These series of plaques were subjected to plaque hybridization using as the probe radiolabeled MC3T3-E1 cDNA for one of the series, and radiolabeled liver cDNA for the other series. In 273 clones, expression was observed with the MC3T3-E1 cDNA probe, but not with the liver cDNA probe. These clones were used as a minilibrary in subsequent experiments.

EXAMPLE 2

Isolation of mouse OSF-5 clone

A description will be made of methods to identify a cDNA fragment of OSF-5 as an MC3T3-E 1 specific clone from the mini-library constructed in Example 1, and to clone full length cDNA from the cDNA library of MC3T3-E1 with the use of this fragment.

The total RNAs from MC3T3-E1 and liver prepared in Example 1 were spotted in an amount of 1 μg each onto nylon membrane filters. 273 of the filters were prepared, and used for hybridization to be described later on. Separately, the DNA of the inserts of the 273 phage clones prepared in Example 1 was amplified by PCR. This DNA was agarose gel electrophoresed, and main bands were lo cut out, purified, and radiolabeled for use as a probe. A clone showing expression with MC3T3-E1 cDNA but no expression with liver cDNA upon autoradiography was recloned into a plasmid vector. Specifically, the DNA of the inserts amplified by PCR and then purified was digested with the restriction enzyme EcoRI, and recloned into the EcoRI site of the plasmid vector pUC118 (Takara Shuzo). The DNA sequence of the resulting clone was determined with commercially available "DNA Sequence Kit" (Takara Shuzo) using a universal primer. Search through DNA and protein data bases showed that DNA sequence to constitute a novel clone dissimilar to the existing DNAs or proteins. This clone was designated as pMCLS68, and used for subsequent cloning of the full length cDNA.

For cloning of the full length cDNA, blund-ended double-stranded cDNA was synthesized with the cDNA synthesis kit "cDNA Synthesis System Plus" (Amersham) using 5 μg of the poly A+RNA of MC3T3-E1 purified in Example 1. The resulting cDNA was ligated to EcoRI/NotI adaptor (Takara Shuzo) using T4 ligase, and the product was agarose gel electrophoresed to purify a fragment more than about 700 base pair long. This fragment was joined to the EcoRI site of lambda gt10 phage vector (Stratagene), and packaged into phage particles in the same way as in Example 1. The packages were infected into E. coil as in Example 1, and the efficiency of infection was determined to be 1.5×10⁷ phage plaques/μg vector DNA. The aforementioned pMCLS68 was radioactively labeled for use as a probe, and 1.0×10⁶ phage clones of the cDNA library were screened by plaque hybridization. Five positive hybridization signals were obtained, whereafter the EcoRI fragment of the phage clone with the longest insert was recloned into the EcoRI site of the plasmid vector pUC118 (Takara Shuzo). The resulting clone was designated as pKOT20.

Example 3

DNA sequence of mouse OSF-5

Deletion mutants of the pKOT20 and a subclone containing its cDNA fragment were prepared with "the Deletion Kit for Kilo Sequence" (Takara Shuzo) by cutting at intervals of 300 base pairs in each opposite direction. The DNA sequence of each deletion mutant was determined with the automatic DNA sequencer 373A (Applied Biosystems, U.S.A.). The entire DNA sequence of the cDNA, and an amino acid sequence translated from this DNA sequence are shown as SEQ. ID NO.: 2 of the Sequence Table. No. 1 of the amino acid residue corresponds to the N-terminus of the predicted OSF-5 precursor protein. The protein encoded by this cDNA was designated as OSF-5. The structure of the resulting mouse OSF-5 protein is schematically shown in FIG. 1, and the restriction enzyme map of the cDNA coding for mouse OSF-5 is shown in FIG. 2. Search through DNA and protein data bases showed that the resulting DNA sequence contained the phospholipid binding domain of blood coagulation factor VIII, as well as domains homologous with all domains of carboxypeptidase H. Alignments of amino acids between mouse OSF-5 and other carboxypeptidase molecules are shown in Tables 1 to 3, and an alignment of amino acids between mouse OSF-5 and the phospholipid binding domains of other blood coagulation factors are shown in Table 4.

Example 4

Tissue specific expression of mouse OSF-5

RNA dot blotting was performed to investigate the tissue specific expression of mouse OSF-5. The total RNAs of the thymus, spleen, brain, kidney, liver, lung, testis and heart of mice (purchased from Nippon Clea) were prepared by the guanidine method. Calvarial osteoblast-rich cells were obtained from a culture of newborn mice calvaria. Total RNA was extracted from these cells in the same way as described above. One μg of the total RNA each from the above-mentioned tissues, calvarial cultured cells, MC3T3-E1 and mouse fibroblast cell line NIH3T3 (ATCC CRL 1658) were dotted onto nylon membrane filters (Biodyne, PALL), fixed by heating, and used for hybridization. Separately, the pKOT20 was digested with SphI, and isolated by agarose gel electrophoresis for purification. Then, the isolate was radioactively labeled and used as a probe. Autoradiography indicated high expression for the calvarial cultured cells and MC3T3-E 1 (FIG. 3).

Example 5

Preparation of anti-OSF-5 antisera

In preparing anti-peptide antibodies against mouse OSF-5, total five peptides, i.e. 11 amino acid residues at the 116th to 126th positions from the N-terminus of the repeating domain, 15 amino acid residues at the 482nd to 496th positions of the blood coagulation factor VIII-like domain, and 15 amino acid residues each at the 557th to 571st, the 701st to 715th, and the 872nd to 886th positions of the carboxypeptidase-like domain, were synthesized by the solid phase synthesis method using a peptide synthesizer (430A, Applied Biosystems). The synthetic peptides were, respectively, OSF-5.1 (KPKEKPPKATK, SEQ. ID No. 6), OSF-5.2 (GYEEMTFYGNVDKDT, SEQ. ID NO.: 7), OSF-5.3 (SYKDMRQLMKAVDEE, SEQ. ID NO.: 8), OSF-5.4 (WAAEEKKWVPYRVPN, SEQ. ID NO.: 9), and OSF-5.5 (PHESELPREWENNKE, SEQ. ID NO:. 10). These synthetic peptides were each joined to ovalbumin using glutaraldehyde as a coupling agent, and used for immunization of rabbits. The resulting antisera could be used to search immunohistochemically nohistochemically for the presence of OSF-5 in newborn mouse systemic slices, and to detect the expression of OSF-5 in E. coil, yeast and animal cells.

Example 6

Expression of OSF-5 in animal cells

NotI fragment containing the cDNA domain of mouse OSF-5 was cloned using pRc/CMV, a vector for expression in animal cells. The resulting plasmid DNA was introduced into Chinese hamster ovarian cells (CHO) by the calcium-phosphate coprecipitation method. The resulting G418-resistant colonies were isolated and proliferated so that each clone was analyzed for OSF-5 expression by Northern blotting analysis. The cloned cells with the highest expression of OSF-5 were analyzed by Western blot analysis, whereby a band with about 80 kilodaltons was detected.

OSF-5 provided by the present invention can be used as an agent for treating bone metabolic diseases, and because of its high organ specificity for bones, it can also be used as a diagnostic reagent for bone metabolic diseases.

TABLE 1

|  | 544 |  |  |  |  |
| --- | --- | --- | --- | --- | --- |
| mOSF-5 | EVVTTDSLDF | RHHSYKDMRQ | LMKAVNEECP | TITRTYSLGK | SSRGLKIYAM |
| bCP-E | .RPQEDGISF | EYHRYPELRE | ALVSVWLQCA | AVSRIYTVGR | SFEGRELLVL |
| rCP-H | RLQQEDGISF | EYHRYPELRE | ALVSVWLQCT | AISRIYTVGR | SFEGRELLVI |
| rCP-E | RLQQEDGISF | EYHRYPELRE | ALVSVWLQCT | AISRIYTVGR | TFEGRELLVI |
| hCP-E | RLQQEDGISF | EYHRYPELRE | ALVSVWLQCT | AISRIYTVGR | SFEGRELLVI |
| hCP-N | .......VTF | RHHRYDDLVR | TLYKVQNECP | GITRVYSIGR | SVEGRHLYVL |
| Consensus | ————————F | —H–Y——— | ——V——C- | ——R–Y—G– | —G——— |
|  | 600 |  |  |  |  |
| mOSF-5 | EISDNPGDHE | LGEPEFRYTA | GIHGNEVLGR | ELLLLLMQYL | CQEYRDGNPR |
| bCP-E | ELSDNPGVHE | PGEPEFKYIG | NMHGNEAVGR | ELLIFLAQYL | CNEYQKGNET |
| rCP-H | ELSDNPGVHE | PGEPEFKYIG | NMHGNEAVGR | ELLIFLAQYL | CNEYQRGNET |
| rCP-E | ELSDNPGVHE | PGEPEFKYIG | NMHGNEAVGR | ELLEFLAQYL | CNEYQRGNET |
| hCP-E | ELSDNPGVHE | PGEPEFKYIG | NMHGNEAVGR | ELLIFLAQYL | CNEYQKGNET |
| hCP-N | EFSDHPHIHE | PLEPEVKYVG | NMHGNEALGR | ELMLQLSEFL | CEEFRNRNQR |
| Consensus | E-SD—PG–HE | —EPE—Y— | —HGNE—GR | EL——L——L | C–E————N–– |
| mOSF-5 | VRNLVQDTRI | HLVPSLNPDG | YEVAAQMGSE | FGNWALGLWT | EEGFDIFEDF |
| bCP-E | IVQLIHNTRI | HIMPSLNPDG | FEKAASQLGE | LKDWFVGRSN | AQGIDLNRNF |
| rCP-H | IVNLIHSTRI | HIMPSLNPDG | FEKAASQPGE | LKDWFVGRSN | AQGIDLNRNF |
| rCP-E | IVNLIHSTRI | HIMPSLNPDG | FEDAASQPGE | LKDWFVGRSN | AQGIDLNRNF |
| hCP-E | IVNLIHSTRI | HIMPSLNPDG | FEKAASQPGE | KLDWFVGRSN | AQGIDLNRNF |
| hCP-N | IVQLIQDTRI | HILPSMNPDG | YEVAAAQGPN | KPGYLVGRNN | ANGVDLNRNF |
| Consensus | ——L——TRI | H—–PS–NPDG | –E-AA——— | ———G—— | —G–D——F |

700

TABLE 1-continued

| | | | | | |
|---|---|---|---|---|---|
| mOSF-5 | PDLNSVLWAA | EEKKWVPYRV | PNNNLPIPE. | .RYLSPDATV | STEVRAIISW |
| bCP-E | PDLDRIVYIN | EKEG.....G | PNNHL.LKNL | KKIVDQNTKL | APETKAVIHW |
| rCP-H | PDLDRIVYVN | EKEG.....G | PNNHL.LKNL | KKIVDQNSKL | APETKAVIHW |
| rCP-E | PDLDRIVYVN | EKEG.....G | PNNHL.LKNL | KKIVDQNSKL | APETKAVIHW |
| hCP-E | PDLDRIVYVN | EKEG.....G | PNNHL.LKNM | KKIVDQNTKL | APETKAVIHW |
| hCP-N | PDLNTYIYYN | EKYG.....G | PNHHLPLPDN | WK.....SQV | EPETRAVIRW |
| Consensus | PDL——— | E——— | PN—L——— | | —E—A—I—W |

TABLE 2

| | | | | | |
|---|---|---|---|---|---|
| mOSF-5 | MEKNPFVLGA | NLNGGERLVS | YPYDMARTPS | QEQLLAEALA | AARGEDDDGV |
| bCP-E | IMDIPFVLSA | NLHGGDLVAN | YPYDET.... | .RSGSAHEYS | S......... |
| rCP-H | IMDIPFVLSA | NLHGGDLVAN | YPYDET.... | .RSGTAHEYS | S......... |
| rCP-E | IMDIPFVLSA | NLHGGDLVAN | YPYDET.... | .RSGTAHEYS | S......... |
| hCP-E | IMDIPFVLSA | NLHGGDLVAN | YPYDET.... | .RSGSAHEYS | S......... |
| hCP-N | MHSFNFVLSA | NLHGGAVVAN | YPYDKSFEHR | VRGVRRTAST | P......... |
| Consensus | ———FVL-A | NL-GG——— | YPYD——— | | |

| | 800 | | | | |
|---|---|---|---|---|---|
| mOSF-5 | SEAQETPDHA | IFRWLAISFA | SAHLTMTEPY | RGGCQAQDYT | SGM..GIVNG |
| bCP-E | .....CPDDD | IFQSLARAYS | SFNPPMSDPD | RPPCRKNDDD | SSFVEGTTNG |
| rCP-H | .....CPDDA | IFQSLARAYS | SFNPVMSDPN | RPPCRKNDDD | SSFVDGTTNG |
| rCP-E | .....CPDDA | IFQSLARAYS | SFNPVMSDPN | RPPCRKNDDD | SSFVDGTTNG |
| hCP-E | .....SPPDA | IFQSLARAYS | SFNPAMSDPN | RPPCRKNDDD | SSFVDGTTNG |
| hCP-N | .....TPDDK | LFQKLAKVYS | YAHGWMFQG. | ......WNCG | DYFPDGITNG |
| Consensus | ———PD— | -F—LA—— | | | ———G—NG |

| | | | | | |
|---|---|---|---|---|---|
| mOSF-5 | AKWNPRSGTF | NDFSYLHTNC | LELSVYLGCD | KFPHESELPR | EWENNKEALL |
| bCP-E | AAWYSVPGGM | QDFNYLSSNC | FEITVELSCE | KFPPEETLKN | YWEDNKNSLI |
| rCP-H | GAWYSVPGGM | QDFNYLSSNC | FEITVELSCE | KFPPEETLKS | YWEDNKNSLI |
| rCP-E | GAWYSVPGGM | QDFNYLSSNC | FEITVELSCE | KFPPEETLKS | YWEDNKNSLI |
| hCP-E | GAWYSVPGGM | QDFNYLSSNC | FEITVELSCE | KFPPEETLKT | YWEDNKNSLI |
| hCP-N | ASWYSLSKGM | QDFNYLHTNC | FEITLELSCD | DFPPEEELQR | EWLGNREALI |
| Consensus | —W——— | -DF—YL—NC | -E———L-C- | KFP-E——L— | -W—N——L- |

| | 900 | | | | |
|---|---|---|---|---|---|
| mOSF-5 | TFMEQVHRGI | KGVVTDEQGI | PIANATISVS | GINHGVKTAS | GGDYWRILNP |
| bCP-E | SYIQQIHRGV | KGFVRDLQGN | PIANATLSVE | GIDHDVTSAK | DGDYWRLLVP |
| rCP-H | NYLEQIHRGV | KGFVRDLQGN | PIANATISVD | GIDHDVTSAK | DGDYWRLLVP |
| rCP-E | NYLEQIHRGV | KGFVRDLQGN | PIANATISVD | GIDHDVTSAK | DGDYWRLLVP |
| hCP-E | SYLEQIHRGV | KGFVRDLQGN | PIANATISVE | GIDHDVTSAK | DGDYWRLLIP |
| hCP-N | QFLEQVHQGI | KGMVLDENYN | NLANAVISVS | GINHDVTSGD | HDGYFRLLLP |
| Consensus | ———Q-H-G- | KG-V-D——— | —ANA—SV- | GI-H-V——— | -GDY-R-L-P |

TABLE 3

| | | | | | |
|---|---|---|---|---|---|
| mOSF-5 | GEYRVTAHAE | GYTSSAKICN | VDYDIGATQC | NFILARSNWK | RIREILAMNG |
| bCP-E | GNYKLTASAP | GYLAIAKKVA | VPYS.PAVRV | DFELES.... | ....F..... |
| rCP-H | GNYKLTASAP | GYLAITKKVA | VPFS.PAVGV | DFELES.... | ....F..... |
| rCP-E | GNYKLTASAP | GYLAITKKVA | VPFS.PAVGV | DFELES.... | ....F..... |
| hCP-E | GNYKLTASAP | GYLAITKKVA | VPYS.PAAGV | DFELES.... | ....F..... |
| hCP-N | GIYTVSATAP | GYDPETVTVT | VGPA.EPTLV | NFHLKR.... | ....SIPQVS |
| Consensus | G-Y——A-A- | GY——— | V——— | -F-L——— | |

| | 1000 | | | | |
|---|---|---|---|---|---|
| mOSF-5 | NRPILGVDPS | RPMTPQQRRM | QQRRLQYRLR | MREQMQLR | (SEQ ID NO:12) |
| bCP-E | .......... | ...SERKEEE | KEELMEWWKM | MSETLNF* | (SEQ ID NO:13) |
| rCP-H | .......... | ...SERKEEE | KEELMEWWKM | MSETLNF* | (SEQ ID NO:14) |
| rCP-E | .......... | ...SERKEEE | KEELMEWWKM | MSETLNF* | (SEQ ID NO:15) |
| hCP-E | .......... | ...SERKEEE | KEELMEWWKM | MSETLNF* | (SEQ ID NO:16) |
| hCP-N | PVRRAPSRRH | GVRAKVQPQA | RKKEMEMRQL | QRGPA*.. | (SEQ ID NO:17) |
| Consensus | ——— | | | | (SEQ ID NO:18) |

TABLE 4

| | 423 | | | 450 | |
|---|---|---|---|---|---|
| mOSF-5 | AWCAED.... | ESQTQWIEVD | TRRTTRFTGV | ITQGRDSSIH | |
| Factor VIII(repeat1) | AWSTKE.... | ..PFSWIKVD | LLAPMIIHGI | KTQGARQKFS | |
| Factor VIII(repeat2) | AWRPQV.... | NNPKEWLQVD | FQKTMKVTGV | TTQGVKSLLT | |
| Factor V(repeat1) | AWSVEKLAAE | FASKPWIQVD | MQKEVIITGI | QTQGAKHYLK | |
| Factor V(repeat2) | AWQAKA.... | NNNKQWLEID | LLKIKKITAI | ITQGCKSLSS | |
| FVIII-SP(repeat1) | AWHASN.... | YDSKPWIQVN | LLRKMRVSGV | MTQGASRAGR | |
| FVIII-SP(repeat2) | AWTAQS.... | NSAKEWLQVD | LGTQRQVTGI | ITQGARDFGH | |
| Discoidin | AWCSSI.... | VDTNQYIVAG | CEVPRTFMCV | ALQGRGD..H | |

TABLE 4-continued

| | | | | | |
|---|---|---|---|---|---|
| Consensus | AW— | —W–VD | L———G— | —TQG— | |
| mOSF-5 | DDFVTTFFVG | FSNDSQTWVM | Y..TNGYEEM | TFYGNVDKDT | SEQ ID NO:19 |
| Factor VIII(repeat1) | SLYISQFIIM | YSLDGKKWQT | YRGNSTGTLM | VFFGNVDSSG | SEQ ID NO:20 |
| Factor VIII(repeat2) | SMYVKEFLIS | SSQDGHQWTL | FFQNGKV..K | VFQGNQDSFT | SEQ ID NO:21 |
| Factor V(repeat1) | SCYTTEFYVA | YSSNGINWQI | FKGNSTRNVM | YFNGNSDAST | SEQ ID NO:22 |
| Factor V(repeat2) | EMYVKSYTIH | YSEQGVEWDP | YRLKSSMVDK | IFEGNTNTKG | SEQ ID NO:23 |
| FVIII-SP(repeat1) | AEYLKTFKVA | YSLDGRKFEF | IQDESGGD.K | EFLGNLDNNS | SEQ ID NO:24 |
| FVIII-SP(repeat2) | IQYVESYKVA | HSDDGVQWTV | YEEQGS..SK | VFQGNLDNNS | SEQ ID NO:25 |
| Discoidin | DQWVTSYKIR | YSLDNVTWSE | YRNGAAIT.. | ...GVTDRNT | SEQ ID NO:26 |
| Consensus | —YV—F— | YS–D——W— | Y———— | –F–GN–D—— | SEQ ID NO:27 |
| | 500 | | | | 531 |
| mOSF-5 | PVLSELPEPV | VARFIRIYPL | TWNGSLCMRL | EVLGC | |
| Factor VIII(repeat1) | IKHNIFNPPI | IARYIRLHPT | HYSIRSTLRM | ELMGC | |
| Factor VIII(repeat2) | PVVNSLDPPL | LTRYLRIHPQ | SWVHGIALRM | EVLGC | |
| Factor V(repeat1) | IKENQFDPPI | VARYIRISPT | RAYNRPTLRL | ELQGC | |
| Factor V(repeat2) | HVKNFFNPPI | ISRFIRVIPK | TWNQSITLRL | ELFGC | |
| FVIII-SP(repeat1) | LKVNMFNPTL | EAQYIRLYPV | SCHRGCTLRF | ELLGC | |
| FVIII-SP(repeat2) | HKKNIFEKPF | MARYVRVLPV | SWHNRITLRL | ELLGC | |
| Discoidin | VVNHFFDTPI | RARSIAIHPL | TWNNHISLRC | EFYTQ | |
| Consensus | ——N–F—P– | –ARYIRI–P– | –W———LRL | ELLGC | |

What is claimed is:

1. DNA coding for a protein comprising OSF-5 having an amino acid sequence at the 26th to 1128th positions in Sequence ID No. 1 of the Sequence Listing.

2. DNA coding for a protein comprising an OSF-5 precursor protein having an amino acid sequence at the 1st to 1128th positions, including a signal peptide at the 1st to 25th positions, in Sequence ID No. 1 of the Sequence Listing.

3. A process for the production of a recombinant mammalian OSF-5 protein, wherein said recombinant mammalian OSF-5 protein comprises an amino acid sequence at the 26th to 1128th positions in Sequence ID No. 1 of the Sequence Listing, comprising the steps of:

(a) obtaining a population of cells containing a DNA composed of the following DNA sequences:

(i) a sequence that can function in the cells to control transcription and translation, and (ii) a DNA sequence joined downstream of said controlling sequence to code for said recombinant protein, and (b) culturing said population of cells under conditions permit the production of said recombinant protein.

4. The process of claim 3 wherein the controlling sequence further contains a DNA coding for signal peptide for secreting said recombinant protein extracellularly such that said DNA is positioned immediately upstream of said DNA sequence coding for said recombinant protein.

5. The process of claim 3 wherein the population of cells is Escherichia coli, or yeast, or mammalian cells.

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 3728 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Mus musculus
        ( B ) STRAIN: osteoblastic cell line MC3T3E1

( i x ) FEATURE:
        ( A ) NAME/KEY: CDS
        ( B ) LOCATION: 69..3452

( x i ) SEQUENCE DESCRIPTION: SEQ ID NO:1:

```
GAATTCGCGG  CCGCCTGCCA  CCCAAGTCCC  TGCTCAAGCC  CGCCCGGCTC  CCGCGCGTGC         60

CCAGAGCC ATG GCT CCA GTG CGC ACC GCA TCC CTG CTC TGC GGC CTC CTG            110
         Met Ala Pro Val Arg Thr Ala Ser Leu Leu Cys Gly Leu Leu
         1               5                  10
```

```
GCA CTG CTG ACG CTG TGC CCT GAG GGG AAC CCA CAG ACG GTG CTG ACG                158
Ala Leu Leu Thr Leu Cys Pro Glu Gly Asn Pro Gln Thr Val Leu Thr
 15              20                  25                  30

GAC GAC GAG ATC GAG GAG TTC CTC GAA GGC TTC CTT TCG GAG TTG GAG                206
Asp Asp Glu Ile Glu Glu Phe Leu Glu Gly Phe Leu Ser Glu Leu Glu
             35                  40                  45

ACC CAG TCC CCG CCC CGG GAA GAC GAC GTG GAA GTC CAG CCG CTT CCC                254
Thr Gln Ser Pro Pro Arg Glu Asp Asp Val Glu Val Gln Pro Leu Pro
             50                  55                  60

GAA CCC ACC CAG CGT CCC CGC AAA TCC AAG GCA GGG GGC AAG CAG CGG                302
Glu Pro Thr Gln Arg Pro Arg Lys Ser Lys Ala Gly Gly Lys Gln Arg
             65                  70                  75

GCA GAT GTA GAA GTC CCT CCA GAA AAA AAC AAA GAC AAA GAG AAG AAA                350
Ala Asp Val Glu Val Pro Pro Glu Lys Asn Lys Asp Lys Glu Lys Lys
         80                  85                  90

GGA AAG AAG GAC AAA GGC CCC AAA GCC ACA AAA CCC CTG GAG GGC TCT                398
Gly Lys Lys Asp Lys Gly Pro Lys Ala Thr Lys Pro Leu Glu Gly Ser
 95              100                 105                 110

ACC AGG CCC ACC AAG AAA CCA AAG GAG AAG CCA CCC AAG GCC ACC AAG                446
Thr Arg Pro Thr Lys Lys Pro Lys Glu Lys Pro Pro Lys Ala Thr Lys
                 115                 120                 125

AAG CCC AAG GAG AAA CCA CCC AAG GCC ACC AAG AAG CCC AAG GAG AAG                494
Lys Pro Lys Glu Lys Pro Pro Lys Ala Thr Lys Lys Pro Lys Glu Lys
             130                 135                 140

CCA CCC AAG GCC ACC AAG AAG CCT AAG GAG AAG CCA CCC AAG GCC ACT                542
Pro Pro Lys Ala Thr Lys Lys Pro Lys Glu Lys Pro Pro Lys Ala Thr
             145                 150                 155

AAG AGG CCC TCG GCA GGA AAG AAG TTC TCA ACT GTG GCC CCC TTG GAA                590
Lys Arg Pro Ser Ala Gly Lys Lys Phe Ser Thr Val Ala Pro Leu Glu
         160                 165                 170

ACG CTG GAT CGG TTA CTC CCC TCA CCC TCC AAC CCC AGC GCC CAG GAG                638
Thr Leu Asp Arg Leu Leu Pro Ser Pro Ser Asn Pro Ser Ala Gln Glu
175              180                 185                 190

CTA CCG CAG AAG AGA GAC ACA CCC TTC CCA AAT GCC TGG CAA GGT CAA                686
Leu Pro Gln Lys Arg Asp Thr Pro Phe Pro Asn Ala Trp Gln Gly Gln
                 195                 200                 205

GGA GAA GAG ACC CAG GTG GAG GCC AAG CAG CCC CGG CCA GAG CCA GAG                734
Gly Glu Glu Thr Gln Val Glu Ala Lys Gln Pro Arg Pro Glu Pro Glu
             210                 215                 220

GAG GAG ACT GAG ATG CCC ACA CTG GAC TAC AAT GAC CAG ATA GAG AAG                782
Glu Glu Thr Glu Met Pro Thr Leu Asp Tyr Asn Asp Gln Ile Glu Lys
         225                 230                 235

GAG GAT TAC GAG GAT TTT AAG TAC ATC CTT TGC CAG AAG CAG CCC AGG                830
Glu Asp Tyr Glu Asp Phe Lys Tyr Ile Leu Cys Gln Lys Gln Pro Arg
240                  245                 250

CCA ACA CCC AGC AGG AGG AGG CTC TGG CCA GAG CGC CCT GAG GAG AAG                878
Pro Thr Pro Ser Arg Arg Arg Leu Trp Pro Glu Arg Pro Glu Glu Lys
255              260                 265                 270

ACT GAA GAG CCA GAG GAA AGG AAG GAA GTC GAG CCA CCT CTG AAG CCC                926
Thr Glu Glu Pro Glu Glu Arg Lys Glu Val Glu Pro Pro Leu Lys Pro
                 275                 280                 285

CTG CTG CCT CCG GAC TAT GGG GAT AGC TAC GTG ATC CCC AAC TAT GAT                974
Leu Leu Pro Pro Asp Tyr Gly Asp Ser Tyr Val Ile Pro Asn Tyr Asp
             290                 295                 300

GAC TTG GAC TAT TAT TTC CCC CAC CCT CCA CCG CAG AAG CCT GAT GTT                1022
Asp Leu Asp Tyr Tyr Phe Pro His Pro Pro Pro Gln Lys Pro Asp Val
         305                 310                 315

GGA CAA GAG GTG GAT GAG GAA AAG GAA GAG ATG AAG AAG CCC AAA AAG                1070
Gly Gln Glu Val Asp Glu Glu Lys Glu Glu Met Lys Lys Pro Lys Lys
```

|     |     |     |     |     |     |     |     |     |     |     |     |     |     |     |     |     |
|---|---|---|---|---|---|---|---|---|---|---|---|---|---|---|---|---|
| | 320 | | | | | 325 | | | | | | 330 | | | | |
| GAG | GGT | AGT | AGC | CCC | AAG | GAG | GAC | ACA | GAG | GAC | AAG | TGG | ACC | GTG | GAG | 1118 |
| Glu | Gly | Ser | Ser | Pro | Lys | Glu | Asp | Thr | Glu | Asp | Lys | Trp | Thr | Val | Glu | |
| 335 | | | | | 340 | | | | | 345 | | | | | 350 | |
| AAA | AAC | AAG | GAC | CAC | AAA | GGG | CCC | CGG | AAG | GGT | GAG | GAG | CTG | GAG | GAG | 1166 |
| Lys | Asn | Lys | Asp | His | Lys | Gly | Pro | Arg | Lys | Gly | Glu | Glu | Leu | Glu | Glu | |
| | | | | 355 | | | | | 360 | | | | | 365 | | |
| GAG | TGG | GCG | CCA | GTG | GAG | AAA | ATC | AAG | TGC | CCA | CCT | ATT | GGG | ATG | GAG | 1214 |
| Glu | Trp | Ala | Pro | Val | Glu | Lys | Ile | Lys | Cys | Pro | Pro | Ile | Gly | Met | Glu | |
| | | | 370 | | | | | 375 | | | | | 380 | | | |
| TCA | CAC | CGC | ATT | GAG | GAC | AAC | CAG | ATC | CGT | GCC | TCC | TCC | ATG | CTG | CGC | 1262 |
| Ser | His | Arg | Ile | Glu | Asp | Asn | Gln | Ile | Arg | Ala | Ser | Ser | Met | Leu | Arg | |
| | | 385 | | | | | 390 | | | | | 395 | | | | |
| CAC | GGC | CTC | GGA | GCC | CAG | CGG | GGC | CGG | CTC | AAC | ATG | CAG | GCT | GGT | GCC | 1310 |
| His | Gly | Leu | Gly | Ala | Gln | Arg | Gly | Arg | Leu | Asn | Met | Gln | Ala | Gly | Ala | |
| | | 400 | | | | | 405 | | | | | 410 | | | | |
| AAT | GAA | GAT | GAC | TAC | TAT | GAC | GGG | GCA | TGG | TGT | GCT | GAG | GAC | GAG | TCG | 1358 |
| Asn | Glu | Asp | Asp | Tyr | Tyr | Asp | Gly | Ala | Trp | Cys | Ala | Glu | Asp | Glu | Ser | |
| 415 | | | | | 420 | | | | | 425 | | | | | 430 | |
| CAG | ACC | CAG | TGG | ATC | GAG | GTG | GAC | ACC | CGA | AGG | ACA | ACT | CGG | TTC | ACG | 1406 |
| Gln | Thr | Gln | Trp | Ile | Glu | Val | Asp | Thr | Arg | Arg | Thr | Thr | Arg | Phe | Thr | |
| | | | | 435 | | | | | 440 | | | | | 445 | | |
| GGC | GTC | ATC | ACT | CAG | GGC | CGT | GAC | TCC | AGC | ATC | CAT | GAC | GAC | TTC | GTG | 1454 |
| Gly | Val | Ile | Thr | Gln | Gly | Arg | Asp | Ser | Ser | Ile | His | Asp | Asp | Phe | Val | |
| | | | 450 | | | | | 455 | | | | | 460 | | | |
| ACT | ACC | TTC | TTT | GTG | GGC | TTC | AGC | AAT | GAC | AGC | CAG | ACC | TGG | GTG | ATG | 1502 |
| Thr | Thr | Phe | Phe | Val | Gly | Phe | Ser | Asn | Asp | Ser | Gln | Thr | Trp | Val | Met | |
| | | 465 | | | | | 470 | | | | | 475 | | | | |
| TAC | ACC | AAT | GGC | TAC | GAG | GAA | ATG | ACC | TTC | TAT | GGA | AAT | GTG | GAC | AAG | 1550 |
| Tyr | Thr | Asn | Gly | Tyr | Glu | Glu | Met | Thr | Phe | Tyr | Gly | Asn | Val | Asp | Lys | |
| | | 480 | | | | | 485 | | | | | 490 | | | | |
| GAC | ACA | CCT | GTG | CTG | AGC | GAG | CTC | CCT | GAG | CCA | GTT | GTG | GCC | CGT | TTC | 1598 |
| Asp | Thr | Pro | Val | Leu | Ser | Glu | Leu | Pro | Glu | Pro | Val | Val | Ala | Arg | Phe | |
| 495 | | | | | 500 | | | | | 505 | | | | | 510 | |
| ATC | CGC | ATC | TAT | CCA | CTC | ACC | TGG | AAC | GGT | AGC | CTG | TGC | ATG | CGC | CTG | 1646 |
| Ile | Arg | Ile | Tyr | Pro | Leu | Thr | Trp | Asn | Gly | Ser | Leu | Cys | Met | Arg | Leu | |
| | | | | 515 | | | | | 520 | | | | | 525 | | |
| GAG | GTG | CTA | GGC | TGC | CCC | GTG | ACC | CCT | GTC | TAC | AGC | TAC | TAC | GCA | CAG | 1694 |
| Glu | Val | Leu | Gly | Cys | Pro | Val | Thr | Pro | Val | Tyr | Ser | Tyr | Tyr | Ala | Gln | |
| | | | 530 | | | | | 535 | | | | | 540 | | | |
| AAT | GAG | GTG | GTA | ACT | ACT | GAC | AGC | CTG | GAC | TTC | CGG | CAC | CAC | AGC | TAC | 1742 |
| Asn | Glu | Val | Val | Thr | Thr | Asp | Ser | Leu | Asp | Phe | Arg | His | His | Ser | Tyr | |
| | | 545 | | | | | 550 | | | | | 555 | | | | |
| AAG | GAC | ATG | CGC | CAG | CTG | ATG | AAG | GCT | GTC | AAT | GAG | GAG | TGC | CCC | ACA | 1790 |
| Lys | Asp | Met | Arg | Gln | Leu | Met | Lys | Ala | Val | Asn | Glu | Glu | Cys | Pro | Thr | |
| | | | 560 | | | | | 565 | | | | | 570 | | | |
| ATC | ACT | CGC | ACA | TAC | AGC | CTG | GGC | AAG | AGT | TCA | CGA | GGG | CTC | AAG | ATC | 1838 |
| Ile | Thr | Arg | Thr | Tyr | Ser | Leu | Gly | Lys | Ser | Ser | Arg | Gly | Leu | Lys | Ile | |
| 575 | | | | | 580 | | | | | 585 | | | | | 590 | |
| TAC | GCA | ATG | GAA | ATC | TCA | GAC | AAC | CCT | GGG | GAT | CAT | GAA | CTG | GGG | GAG | 1886 |
| Tyr | Ala | Met | Glu | Ile | Ser | Asp | Asn | Pro | Gly | Asp | His | Glu | Leu | Gly | Glu | |
| | | | | 595 | | | | | 600 | | | | | 605 | | |
| CCC | GAG | TTC | CGC | TAC | ACA | GCC | GGG | ATC | CAC | GGC | AAT | GAG | GTG | CTA | GGC | 1934 |
| Pro | Glu | Phe | Arg | Tyr | Thr | Ala | Gly | Ile | His | Gly | Asn | Glu | Val | Leu | Gly | |
| | | | 610 | | | | | 615 | | | | | 620 | | | |
| CGA | GAG | CTC | CTG | CTC | CTG | CTC | ATG | CAA | TAC | CTA | TGC | CAG | GAG | TAC | CGC | 1982 |
| Arg | Glu | Leu | Leu | Leu | Leu | Leu | Met | Gln | Tyr | Leu | Cys | Gln | Glu | Tyr | Arg | |
| | | 625 | | | | | 630 | | | | | 635 | | | | |
| GAT | GGG | AAC | CCG | AGA | GTG | CGC | AAC | CTG | GTG | CAG | GAC | ACA | CGC | ATC | CAC | 2030 |

-continued

| | | | | | | | | | | | | | | |
|---|---|---|---|---|---|---|---|---|---|---|---|---|---|---|
|Asp|Gly|Asn|Pro|Arg|Val|Arg|Asn|Leu|Val|Gln|Asp|Thr|Arg|Ile|His|
| |640| | | |645| | | |650| | | | | | |

| CTG | GTG | CCC | TCG | CTG | AAC | CCT | GAT | GGC | TAT | GAG | GTG | GCA | GCG | CAG | ATG | 2078 |
|---|---|---|---|---|---|---|---|---|---|---|---|---|---|---|---|---|
| Leu | Val | Pro | Ser | Leu | Asn | Pro | Asp | Gly | Tyr | Glu | Val | Ala | Ala | Gln | Met |  |
| 655 |  |  |  | 660 |  |  |  |  | 665 |  |  |  |  |  | 670 |  |

| GGC | TCA | GAG | TTT | GGG | AAC | TGG | GCA | CTG | GGG | CTG | TGG | ACT | GAG | GAG | GGC | 2126 |
|---|---|---|---|---|---|---|---|---|---|---|---|---|---|---|---|---|
| Gly | Ser | Glu | Phe | Gly | Asn | Trp | Ala | Leu | Gly | Leu | Trp | Thr | Glu | Glu | Gly |  |
|  |  |  |  | 675 |  |  |  |  | 680 |  |  |  |  | 685 |  |  |

| TTT | GAC | ATC | TTC | GAG | GAC | TTC | CCA | GAT | CTC | AAC | TCT | GTG | CTC | TGG | GCA | 2174 |
|---|---|---|---|---|---|---|---|---|---|---|---|---|---|---|---|---|
| Phe | Asp | Ile | Phe | Glu | Asp | Phe | Pro | Asp | Leu | Asn | Ser | Val | Leu | Trp | Ala |  |
|  |  |  | 690 |  |  |  | 695 |  |  |  |  | 700 |  |  |  |  |

| GCT | GAG | GAG | AAG | AAA | TGG | GTC | CCC | TAC | AGG | GTC | CCA | AAC | AAT | AAC | TTG | 2222 |
|---|---|---|---|---|---|---|---|---|---|---|---|---|---|---|---|---|
| Ala | Glu | Glu | Lys | Lys | Trp | Val | Pro | Tyr | Arg | Val | Pro | Asn | Asn | Asn | Leu |  |
|  |  | 705 |  |  |  |  | 710 |  |  |  |  | 715 |  |  |  |  |

| CCA | ATC | CCT | GAA | CGT | TAC | CTG | TCC | CCA | GAT | GCC | ACG | GTC | TCC | ACA | GAA | 2270 |
|---|---|---|---|---|---|---|---|---|---|---|---|---|---|---|---|---|
| Pro | Ile | Pro | Glu | Arg | Tyr | Leu | Ser | Pro | Asp | Ala | Thr | Val | Ser | Thr | Glu |  |
| 720 |  |  |  |  | 725 |  |  |  |  | 730 |  |  |  |  |  |  |

| GTC | CGG | GCC | ATT | ATT | TCC | TGG | ATG | GAG | AAG | AAC | CCC | TTT | GTG | CTG | GGT | 2318 |
|---|---|---|---|---|---|---|---|---|---|---|---|---|---|---|---|---|
| Val | Arg | Ala | Ile | Ile | Ser | Trp | Met | Glu | Lys | Asn | Pro | Phe | Val | Leu | Gly |  |
| 735 |  |  |  |  | 740 |  |  |  |  | 745 |  |  |  |  | 750 |  |

| GCA | AAT | CTG | AAC | GGT | GGT | GAG | CGG | CTT | GTG | TCT | TAT | CCC | TAT | GAC | ATG | 2366 |
|---|---|---|---|---|---|---|---|---|---|---|---|---|---|---|---|---|
| Ala | Asn | Leu | Asn | Gly | Gly | Glu | Arg | Leu | Val | Ser | Tyr | Pro | Tyr | Asp | Met |  |
|  |  |  |  | 755 |  |  |  |  | 760 |  |  |  |  | 765 |  |  |

| GCC | CGG | ACA | CCT | AGC | CAG | GAG | CAG | CTG | TTG | GCC | GAG | GCA | CTG | GCA | GCT | 2414 |
|---|---|---|---|---|---|---|---|---|---|---|---|---|---|---|---|---|
| Ala | Arg | Thr | Pro | Ser | Gln | Glu | Gln | Leu | Leu | Ala | Glu | Ala | Leu | Ala | Ala |  |
|  |  |  | 770 |  |  |  |  | 775 |  |  |  |  | 780 |  |  |  |

| GCC | CGC | GGA | GAA | GAT | GAT | GAC | GGG | GTG | TCT | GAG | GCC | CAG | GAG | ACT | CCA | 2462 |
|---|---|---|---|---|---|---|---|---|---|---|---|---|---|---|---|---|
| Ala | Arg | Gly | Glu | Asp | Asp | Asp | Gly | Val | Ser | Glu | Ala | Gln | Glu | Thr | Pro |  |
|  |  | 785 |  |  |  |  | 790 |  |  |  |  | 795 |  |  |  |  |

| GAT | CAC | GCT | ATT | TTC | CGC | TGG | CTG | GCC | ATC | TCA | TTT | GCC | TCC | GCC | CAT | 2510 |
|---|---|---|---|---|---|---|---|---|---|---|---|---|---|---|---|---|
| Asp | His | Ala | Ile | Phe | Arg | Trp | Leu | Ala | Ile | Ser | Phe | Ala | Ser | Ala | His |  |
| 800 |  |  |  |  | 805 |  |  |  |  | 810 |  |  |  |  |  |  |

| CTC | ACC | ATG | ACG | GAG | CCC | TAC | CGG | GGA | GGG | TGC | CAG | GCC | CAG | GAC | TAC | 2558 |
|---|---|---|---|---|---|---|---|---|---|---|---|---|---|---|---|---|
| Leu | Thr | Met | Thr | Glu | Pro | Tyr | Arg | Gly | Gly | Cys | Gln | Ala | Gln | Asp | Tyr |  |
| 815 |  |  |  |  | 820 |  |  |  |  | 825 |  |  |  |  | 830 |  |

| ACC | AGC | GGC | ATG | GGC | ATT | GTC | AAC | GGG | GCC | AAG | TGG | AAT | CCT | CGC | TCT | 2606 |
|---|---|---|---|---|---|---|---|---|---|---|---|---|---|---|---|---|
| Thr | Ser | Gly | Met | Gly | Ile | Val | Asn | Gly | Ala | Lys | Trp | Asn | Pro | Arg | Ser |  |
|  |  |  |  | 835 |  |  |  |  | 840 |  |  |  |  | 845 |  |  |

| GGG | ACT | TTC | AAT | GAC | TTT | AGC | TAC | CTG | CAC | ACA | AAC | TGT | CTG | GAG | CTC | 2654 |
|---|---|---|---|---|---|---|---|---|---|---|---|---|---|---|---|---|
| Gly | Thr | Phe | Asn | Asp | Phe | Ser | Tyr | Leu | His | Thr | Asn | Cys | Leu | Glu | Leu |  |
|  |  |  | 850 |  |  |  |  | 855 |  |  |  |  | 860 |  |  |  |

| TCC | GTA | TAC | CTG | GGC | TGT | GAC | AAG | TTC | CCC | CAC | GAG | AGT | GAG | CTA | CCC | 2702 |
|---|---|---|---|---|---|---|---|---|---|---|---|---|---|---|---|---|
| Ser | Val | Tyr | Leu | Gly | Cys | Asp | Lys | Phe | Pro | His | Glu | Ser | Glu | Leu | Pro |  |
|  |  | 865 |  |  |  |  | 870 |  |  |  |  | 875 |  |  |  |  |

| CGA | GAA | TGG | GAG | AAC | AAC | AAA | GAA | GCG | CTG | CTC | ACC | TTC | ATG | GAG | CAG | 2750 |
|---|---|---|---|---|---|---|---|---|---|---|---|---|---|---|---|---|
| Arg | Glu | Trp | Glu | Asn | Asn | Lys | Glu | Ala | Leu | Leu | Thr | Phe | Met | Glu | Gln |  |
| 880 |  |  |  |  | 885 |  |  |  |  | 890 |  |  |  |  |  |  |

| GTG | CAC | CGT | GGC | ATT | AAG | GGT | GTG | ACA | GAT | GAG | CAA | GGC | ATC | CCC | | 2798 |
|---|---|---|---|---|---|---|---|---|---|---|---|---|---|---|---|---|
| Val | His | Arg | Gly | Ile | Lys | Gly | Val | Val | Thr | Asp | Glu | Gln | Gly | Ile | Pro |  |
| 895 |  |  |  |  | 900 |  |  |  |  | 905 |  |  |  |  | 910 |  |

| ATT | GCC | AAT | GCC | ACC | ATC | TCT | GTG | AGT | GGC | ATC | AAC | CAT | GGT | GTG | AAG | 2846 |
|---|---|---|---|---|---|---|---|---|---|---|---|---|---|---|---|---|
| Ile | Ala | Asn | Ala | Thr | Ile | Ser | Val | Ser | Gly | Ile | Asn | His | Gly | Val | Lys |  |
|  |  |  |  | 915 |  |  |  |  | 920 |  |  |  |  | 925 |  |  |

| ACA | GCA | AGT | GGA | GGT | GAC | TAC | TGG | CGC | ATT | CTG | AAC | CCG | GGT | GAG | TAC | 2894 |
|---|---|---|---|---|---|---|---|---|---|---|---|---|---|---|---|---|
| Thr | Ala | Ser | Gly | Gly | Asp | Tyr | Trp | Arg | Ile | Leu | Asn | Pro | Gly | Glu | Tyr |  |
|  |  |  | 930 |  |  |  |  | 935 |  |  |  |  | 940 |  |  |  |

| CGT | GTG | ACA | GCT | CAC | GCA | GAG | GGC | TAC | ACC | TCA | AGT | GCC | AAG | ATC | TGC | 2942 |
|---|---|---|---|---|---|---|---|---|---|---|---|---|---|---|---|---|
| Arg | Val | Thr | Ala | His | Ala | Glu | Gly | Tyr | Thr | Ser | Ser | Ala | Lys | Ile | Cys |  |
|  |  | 945 |  |  |  |  | 950 |  |  |  |  | 955 |  |  |  |  |

| | | | | | | | | | | | | | | | | |
|---|---|---|---|---|---|---|---|---|---|---|---|---|---|---|---|---|
| AAT | GTG | GAC | TAC | GAT | ATT | GGG | GCC | ACT | CAG | TGC | AAC | TTC | ATC | CTG | GCT | 2990 |
| Asn | Val | Asp | Tyr | Asp | Ile | Gly | Ala | Thr | Gln | Cys | Asn | Phe | Ile | Leu | Ala | |
| | 960 | | | | 965 | | | | | 970 | | | | | | |
| CGA | TCC | AAC | TGG | AAG | CGC | ATT | CGG | GAG | ATC | TTG | GCT | ATG | AAC | GGG | AAC | 3038 |
| Arg | Ser | Asn | Trp | Lys | Arg | Ile | Arg | Glu | Ile | Leu | Ala | Met | Asn | Gly | Asn | |
| 975 | | | | | 980 | | | | | 985 | | | | | 990 | |
| CGT | CCC | ATT | CTC | GGA | GTT | GAC | CCC | TCA | CGA | CCC | ATG | ACC | CCC | CAG | CAG | 3086 |
| Arg | Pro | Ile | Leu | Gly | Val | Asp | Pro | Ser | Arg | Pro | Met | Thr | Pro | Gln | Gln | |
| | | | | 995 | | | | | 1000 | | | | | 1005 | | |
| CGG | CGC | ATG | CAG | CAG | CGC | CGT | CTA | CAG | TAC | CGG | CTC | CGC | ATG | AGG | GAA | 3134 |
| Arg | Arg | Met | Gln | Gln | Arg | Arg | Leu | Gln | Tyr | Arg | Leu | Arg | Met | Arg | Glu | |
| | | | 1010 | | | | | 1015 | | | | | 1020 | | | |
| CAG | ATG | CAA | CTG | CGT | CGC | CTC | AAT | TCT | ACC | GCA | GGC | CCT | GCC | ACA | AGC | 3182 |
| Gln | Met | Gln | Leu | Arg | Arg | Leu | Asn | Ser | Thr | Ala | Gly | Pro | Ala | Thr | Ser | |
| | | | 1025 | | | | | 1030 | | | | | 1035 | | | |
| CCC | ACT | CCT | GCC | CTT | ATG | CCT | CCC | CCT | TCC | CCT | ACA | CCA | GCC | ATT | ACC | 3230 |
| Pro | Thr | Pro | Ala | Leu | Met | Pro | Pro | Pro | Ser | Pro | Thr | Pro | Ala | Ile | Thr | |
| | | | 1040 | | | | | 1045 | | | | | 1050 | | | |
| TTG | AGG | CCC | TGG | GAA | GTT | CTA | CCC | ACT | ACC | ACT | GCA | GGC | TGG | GAG | GAG | 3278 |
| Leu | Arg | Pro | Trp | Glu | Val | Leu | Pro | Thr | Thr | Thr | Ala | Gly | Trp | Glu | Glu | |
| 1055 | | | | | 1060 | | | | | 1065 | | | | | 1070 | |
| TCA | GAG | ACT | GAG | ACC | TAT | ACA | GAA | GTA | GTG | ACA | GAG | TTT | GAG | ACA | GAG | 3326 |
| Ser | Glu | Thr | Glu | Thr | Tyr | Thr | Glu | Val | Val | Thr | Glu | Phe | Glu | Thr | Glu | |
| | | | | | 1075 | | | | | 1080 | | | | | 1085 | |
| TAT | GGG | ACT | GAC | CTA | GAG | GTG | GAA | GAG | ATA | GAG | GAG | GAG | GAG | GAG | GAG | 3374 |
| Tyr | Gly | Thr | Asp | Leu | Glu | Val | Glu | Glu | Ile | Glu | Glu | Glu | Glu | Glu | Glu | |
| | | | 1090 | | | | | 1095 | | | | | 1100 | | | |
| GAG | GAG | GAA | GAG | ATG | GAC | ACA | GGC | CTT | ACA | TTT | CCA | CTC | ACA | ACA | GTG | 3422 |
| Glu | Glu | Glu | Glu | Met | Asp | Thr | Gly | Leu | Thr | Phe | Pro | Leu | Thr | Thr | Val | |
| | | | 1105 | | | | | 1110 | | | | | 1115 | | | |
| GAG | ACC | TAC | ACA | GTG | AAC | TTT | GGG | GAC | TTC | TGAGACTGGG | ATCTCAAAGC | | | | | 3472 |
| Glu | Thr | Tyr | Thr | Val | Asn | Phe | Gly | Asp | Phe | | | | | | | |
| | 1120 | | | | | 1125 | | | | | | | | | | |

| | | | | | |
|---|---|---|---|---|---|
| CCTGCCCAAT | TCAAACTAAG | GCAGCACCTC | CCAAGCCTGT | GCCAGCAGAC | ACATAGCCAT | 3532 |
| CAGATGTCCC | TGGGGTGGAC | CCCACTCCCC | CAGTGTGGGA | CATCAAAGCT | ACCGGGACTC | 3592 |
| TGCATAGACT | CTGGTCTACC | CGCCCCAGCT | CTTACCTGCC | AGCCTTTGGG | GGAGGGGCAG | 3652 |
| GCAAAGGAAG | CCAACGTTCA | ACATCAATAA | AACCAAGCTC | ATGACACCAA | AAAAAAAAA | 3712 |
| AAGCGGCCGC | GAATTC | | | | | 3728 |

( 2 ) INFORMATION FOR SEQ ID NO:2:

( i ) SEQUENCE CHARACTERISTICS:
        ( A ) LENGTH: 1128 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Ala | Pro | Val | Arg | Thr | Ala | Ser | Leu | Leu | Cys | Gly | Leu | Leu | Ala | Leu |
| 1 | | | | 5 | | | | | 10 | | | | | 15 | |
| Leu | Thr | Leu | Cys | Pro | Glu | Gly | Asn | Pro | Gln | Thr | Val | Leu | Thr | Asp | Asp |
| | | | 20 | | | | | 25 | | | | | 30 | | |
| Glu | Ile | Glu | Glu | Phe | Leu | Glu | Gly | Phe | Leu | Ser | Glu | Leu | Glu | Thr | Gln |
| | | 35 | | | | | 40 | | | | | 45 | | | |
| Ser | Pro | Pro | Arg | Glu | Asp | Asp | Val | Glu | Val | Gln | Pro | Leu | Pro | Glu | Pro |
| | 50 | | | | | 55 | | | | | 60 | | | | |
| Thr | Gln | Arg | Pro | Arg | Lys | Ser | Lys | Ala | Gly | Gly | Lys | Gln | Arg | Ala | Asp |

|     |     |     |     |     |     |     |     |     |     |     |     |     |     |     |     |
| --- | --- | --- | --- | --- | --- | --- | --- | --- | --- | --- | --- | --- | --- | --- | --- |
| 65  |     |     |     |     | 70  |     |     |     |     | 75  |     |     |     |     | 80  |
| Val | Glu | Val | Pro | Pro<br>85 | Glu | Lys | Asn | Lys | Asp<br>90 | Lys | Glu | Lys | Lys | Gly<br>95 | Lys |
| Lys | Asp | Lys | Gly<br>100 | Pro | Lys | Ala | Thr | Lys<br>105 | Pro | Leu | Glu | Gly<br>110 | Ser | Thr | Arg |
| Pro | Thr | Lys<br>115 | Lys | Pro | Lys | Glu | Lys<br>120 | Pro | Pro | Lys | Ala | Thr<br>125 | Lys | Lys | Pro |
| Lys | Glu<br>130 | Lys | Pro | Pro | Lys | Ala<br>135 | Thr | Lys | Lys | Pro | Lys<br>140 | Glu | Lys | Pro | Pro |
| Lys<br>145 | Ala | Thr | Lys | Lys | Pro<br>150 | Lys | Glu | Lys | Pro | Pro<br>155 | Lys | Ala | Thr | Lys | Arg<br>160 |
| Pro | Ser | Ala | Gly | Lys<br>165 | Lys | Phe | Ser | Thr | Val<br>170 | Ala | Pro | Leu | Glu | Thr<br>175 | Leu |
| Asp | Arg | Leu | Leu<br>180 | Pro | Ser | Pro | Ser | Asn<br>185 | Pro | Ser | Ala | Gln | Glu<br>190 | Leu | Pro |
| Gln | Lys | Arg<br>195 | Asp | Thr | Pro | Phe | Pro<br>200 | Asn | Ala | Trp | Gln | Gly<br>205 | Gln | Gly | Glu |
| Glu | Thr<br>210 | Gln | Val | Glu | Ala | Lys<br>215 | Gln | Pro | Arg | Pro | Glu<br>220 | Pro | Glu | Glu | Glu |
| Thr<br>225 | Glu | Met | Pro | Thr | Leu<br>230 | Asp | Tyr | Asn | Asp | Gln<br>235 | Ile | Glu | Lys | Glu | Asp<br>240 |
| Tyr | Glu | Asp | Phe | Lys<br>245 | Tyr | Ile | Leu | Cys | Gln<br>250 | Lys | Gln | Pro | Arg | Pro<br>255 | Thr |
| Pro | Ser | Arg | Arg<br>260 | Arg | Leu | Trp | Pro | Glu<br>265 | Arg | Pro | Glu | Glu | Lys<br>270 | Thr | Glu |
| Glu | Pro | Glu<br>275 | Glu | Arg | Lys | Glu | Val<br>280 | Glu | Pro | Pro | Leu | Lys<br>285 | Pro | Leu | Leu |
| Pro | Pro<br>290 | Asp | Tyr | Gly | Asp | Ser<br>295 | Tyr | Val | Ile | Pro | Asn<br>300 | Tyr | Asp | Asp | Leu |
| Asp<br>305 | Tyr | Tyr | Phe | Pro | His<br>310 | Pro | Pro | Pro | Gln | Lys<br>315 | Pro | Asp | Val | Gly | Gln<br>320 |
| Glu | Val | Asp | Glu | Glu<br>325 | Lys | Glu | Glu | Met | Lys<br>330 | Lys | Pro | Lys | Lys | Glu<br>335 | Gly |
| Ser | Ser | Pro | Lys<br>340 | Glu | Asp | Thr | Glu | Asp<br>345 | Lys | Trp | Thr | Val | Glu<br>350 | Lys | Asn |
| Lys | Asp | His<br>355 | Lys | Gly | Pro | Arg | Lys<br>360 | Gly | Glu | Glu | Leu | Glu<br>365 | Glu | Glu | Trp |
| Ala | Pro<br>370 | Val | Glu | Lys | Ile | Lys<br>375 | Cys | Pro | Pro | Ile | Gly<br>380 | Met | Glu | Ser | His |
| Arg<br>385 | Ile | Glu | Asp | Asn | Gln<br>390 | Ile | Arg | Ala | Ser | Ser<br>395 | Met | Leu | Arg | His | Gly<br>400 |
| Leu | Gly | Ala | Gln | Arg<br>405 | Gly | Arg | Leu | Asn | Met<br>410 | Gln | Ala | Gly | Ala | Asn<br>415 | Glu |
| Asp | Asp | Tyr | Tyr<br>420 | Asp | Gly | Ala | Trp | Cys<br>425 | Ala | Glu | Asp | Glu | Ser<br>430 | Gln | Thr |
| Gln | Trp | Ile<br>435 | Glu | Val | Asp | Thr | Arg<br>440 | Arg | Thr | Thr | Arg | Phe<br>445 | Thr | Gly | Val |
| Ile | Thr<br>450 | Gln | Gly | Arg | Asp | Ser<br>455 | Ser | Ile | His | Asp | Asp<br>460 | Phe | Val | Thr | Thr |
| Phe<br>465 | Phe | Val | Gly | Phe | Ser<br>470 | Asn | Asp | Ser | Gln | Thr<br>475 | Trp | Val | Met | Tyr | Thr<br>480 |
| Asn | Gly | Tyr | Glu | Glu<br>485 | Met | Thr | Phe | Tyr | Gly<br>490 | Asn | Val | Asp | Lys | Asp<br>495 | Thr |

-continued

| | | | | | | | | | | | | | | |
|---|---|---|---|---|---|---|---|---|---|---|---|---|---|---|
|Pro|Val|Leu|Ser<br>500|Glu|Leu|Pro|Glu|Pro<br>505|Val|Val|Ala|Arg|Phe<br>510|Ile|Arg|
|Ile|Tyr|Pro<br>515|Leu|Thr|Trp|Asn|Ser<br>520|Leu|Cys|Met|Arg<br>525|Leu|Glu|Val| |
|Leu|Gly<br>530|Cys|Pro|Val|Thr|Pro<br>535|Val|Tyr|Ser|Tyr|Tyr<br>540|Ala|Gln|Asn|Glu|
|Val<br>545|Val|Thr|Thr|Asp|Ser<br>550|Leu|Asp|Phe|Arg|His<br>555|His|Ser|Tyr|Lys|Asp<br>560|
|Met|Arg|Gln|Leu|Met<br>565|Lys|Ala|Val|Asn|Glu<br>570|Glu|Cys|Pro|Thr|Ile<br>575|Thr|
|Arg|Thr|Tyr|Ser<br>580|Leu|Gly|Lys|Ser|Ser<br>585|Arg|Gly|Leu|Lys|Ile<br>590|Tyr|Ala|
|Met|Glu|Ile<br>595|Ser|Asp|Asn|Pro|Gly<br>600|Asp|His|Glu|Leu|Gly<br>605|Glu|Pro|Glu|
|Phe|Arg<br>610|Tyr|Thr|Ala|Gly|Ile<br>615|His|Gly|Asn|Glu|Val<br>620|Leu|Gly|Arg|Glu|
|Leu<br>625|Leu|Leu|Leu|Leu|Met<br>630|Gln|Tyr|Leu|Cys|Gln<br>635|Glu|Tyr|Arg|Asp|Gly<br>640|
|Asn|Pro|Arg|Val|Arg<br>645|Asn|Leu|Val|Gln|Asp<br>650|Thr|Arg|Ile|His|Leu<br>655|Val|
|Pro|Ser|Leu|Asn<br>660|Pro|Asp|Gly|Tyr|Glu<br>665|Val|Ala|Ala|Gln|Met<br>670|Gly|Ser|
|Glu|Phe|Gly<br>675|Asn|Trp|Ala|Leu|Gly<br>680|Leu|Trp|Thr|Glu|Glu<br>685|Gly|Phe|Asp|
|Ile|Phe<br>690|Glu|Asp|Phe|Pro|Asp<br>695|Leu|Asn|Ser|Val|Leu<br>700|Trp|Ala|Ala|Glu|
|Glu<br>705|Lys|Lys|Trp|Val|Pro<br>710|Tyr|Arg|Val|Pro|Asn<br>715|Asn|Asn|Leu|Pro|Ile<br>720|
|Pro|Glu|Arg|Tyr|Leu<br>725|Ser|Pro|Asp|Ala|Thr<br>730|Val|Ser|Thr|Glu|Val<br>735|Arg|
|Ala|Ile|Ile|Ser<br>740|Trp|Met|Glu|Lys|Asn<br>745|Pro|Phe|Val|Leu|Gly<br>750|Ala|Asn|
|Leu|Asn|Gly<br>755|Gly|Glu|Arg|Leu|Val<br>760|Ser|Tyr|Pro|Tyr|Asp<br>765|Met|Ala|Arg|
|Thr|Pro<br>770|Ser|Gln|Glu|Gln|Leu<br>775|Leu|Ala|Glu|Ala|Leu<br>780|Ala|Ala|Ala|Arg|
|Gly<br>785|Glu|Asp|Asp|Asp|Gly<br>790|Val|Ser|Glu|Ala|Gln<br>795|Glu|Thr|Pro|Asp|His<br>800|
|Ala|Ile|Phe|Arg|Trp<br>805|Leu|Ala|Ile|Ser|Phe<br>810|Ala|Ser|Ala|His|Leu<br>815|Thr|
|Met|Thr|Glu|Pro<br>820|Tyr|Arg|Gly|Gly|Cys<br>825|Gln|Ala|Gln|Asp|Tyr<br>830|Thr|Ser|
|Gly|Met|Gly<br>835|Ile|Val|Asn|Gly|Ala<br>840|Lys|Trp|Asn|Pro|Arg<br>845|Ser|Gly|Thr|
|Phe|Asn<br>850|Asp|Phe|Ser|Tyr|Leu<br>855|His|Thr|Asn|Cys|Leu<br>860|Glu|Leu|Ser|Val|
|Tyr<br>865|Leu|Gly|Cys|Asp|Lys<br>870|Phe|Pro|His|Glu|Ser<br>875|Glu|Leu|Pro|Arg|Glu<br>880|
|Trp|Glu|Asn|Asn|Lys<br>885|Glu|Ala|Leu|Leu|Thr<br>890|Phe|Met|Glu|Gln|Val<br>895|His|
|Arg|Gly|Ile|Lys<br>900|Gly|Val|Val|Thr|Asp<br>905|Glu|Gln|Gly|Ile|Pro<br>910|Ile|Ala|

```
Asn  Ala  Thr  Ile  Ser  Val  Ser  Gly  Ile  Asn  His  Gly  Val  Lys  Thr  Ala
          915                      920                     925

Ser  Gly  Gly  Asp  Tyr  Trp  Arg  Ile  Leu  Asn  Pro  Gly  Glu  Tyr  Arg  Val
          930                      935                     940

Thr  Ala  His  Ala  Glu  Gly  Tyr  Thr  Ser  Ser  Ala  Lys  Ile  Cys  Asn  Val
945                           950                     955                     960

Asp  Tyr  Asp  Ile  Gly  Ala  Thr  Gln  Cys  Asn  Phe  Ile  Leu  Ala  Arg  Ser
                    965                      970                     975

Asn  Trp  Lys  Arg  Ile  Arg  Glu  Ile  Leu  Ala  Met  Asn  Gly  Asn  Arg  Pro
               980                      985                     990

Ile  Leu  Gly  Val  Asp  Pro  Ser  Arg  Pro  Met  Thr  Pro  Gln  Gln  Arg  Arg
          995                      1000                    1005

Met  Gln  Gln  Arg  Arg  Leu  Gln  Tyr  Arg  Leu  Arg  Met  Arg  Glu  Gln  Met
     1010                     1015                    1020

Gln  Leu  Arg  Arg  Leu  Asn  Ser  Thr  Ala  Gly  Pro  Ala  Thr  Ser  Pro  Thr
1025                     1030                     1035                    1040

Pro  Ala  Leu  Met  Pro  Pro  Ser  Pro  Thr  Pro  Ala  Ile  Thr  Leu  Arg
               1045                     1050                    1055

Pro  Trp  Glu  Val  Leu  Pro  Thr  Thr  Thr  Ala  Gly  Trp  Glu  Glu  Ser  Glu
               1060                     1065                    1070

Thr  Glu  Thr  Tyr  Thr  Glu  Val  Val  Thr  Glu  Phe  Glu  Thr  Glu  Tyr  Gly
          1075                     1080                    1085

Thr  Asp  Leu  Glu  Val  Glu  Glu  Ile  Glu  Glu  Glu  Glu  Glu  Glu  Glu  Glu
     1090                     1095                     1100

Glu  Glu  Met  Asp  Thr  Gly  Leu  Thr  Phe  Pro  Leu  Thr  Thr  Val  Glu  Thr
1105                     1110                     1115                    1120

Tyr  Thr  Val  Asn  Phe  Gly  Asp  Phe
                    1125
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: linker DNA with sequence complementary
          to Sequence ID No. 4, termed "ATOS-1"

( x i ) SEQUENCE DESCRIPTION: SEQ ID NO:3:

CTCTTGCTTG AATTCGGACT A                                                        21

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: linker DNA with sequence complementary
          to Sequence ID No. 3, termed "ATOS-2"

( x i ) SEQUENCE DESCRIPTION: SEQ ID NO:4:

TAGTCCGAAT TCAAGCAAGA GCACA                                              25

( 2 ) INFORMATION FOR SEQ ID NO:5:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Other
    ( A ) DESCRIPTION: linker DNA with sequence complementary
        to Sequence ID No. 6, termed "ATOS-4"

( x i ) SEQUENCE DESCRIPTION: SEQ ID NO:5:

CTCTTGCTTA AGCTTGGACT A                                                   21

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: linker DNA with sequence complementary
            to Sequence ID No. 5, termed "ATOS-5"

( x i ) SEQUENCE DESCRIPTION: SEQ ID NO:6:

TAGTCCAAGC TTAAGCAAGA GCACA                                               25

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: Other
        ( A ) DESCRIPTION: OSF 5.1 (antigen peptide)
            segment of mouse OSF-5 from the 116th to
            the 126th amino acid residue ( v i ) ORIGINAL SOURCE:
        ( A ) ORGANISM: Mus musculus ( x i ) SEQUENCE DESCRIPTION: SEQ ID NO:7:

Lys Pro Lys Glu Lys Pro Pro Lys Ala Thr Lys
1               5                   10

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: Other
        ( A ) DESCRIPTION: OSF 5.1 (antigen peptide)
            segment of mouse OSF-5 from the 482nd to
            the 496th amino acid residue ( v i ) ORIGINAL SOURCE:
        ( A ) ORGANISM: Mus musculus ( x i ) SEQUENCE DESCRIPTION: SEQ ID NO:8:

Gly Thr Gln Gln Met Thr Phe Tyr Gly Asn Val Asp Lys Asp Thr
1               5                   10                  15

( 2 ) INFORMATION FOR SEQ ID NO:9:

( i ) SEQUENCE CHARACTERISTICS:
        ( A ) LENGTH: 15 amino acids
        ( B ) TYPE: amino acid ( D ) TOPOLOGY: linear ( i i ) MOLECULE TYPE: Other
        ( A ) DESCRIPTION: OSF 5.1 (antigen peptide)
            segment of mouse OSF-5 from the 557th to
            the 571st amino acid residue ( v i ) ORIGINAL SOURCE:
        ( A ) ORGANISM: Mus musculus ( x i ) SEQUENCE DESCRIPTION: SEQ ID NO:9:

Ser  Tyr  Lys  Asp  Met  Arg  Gln  Leu  Met  Lys  Ala  Val  Asp  Glu  Glu
    1                   5                        10                       15

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: Other
        ( A ) DESCRIPTION: OSF 5.1 (antigen peptide)
            segment of mouse OSF-5 from the 701st to
            the 715th amino acid residue ( v i ) ORIGINAL SOURCE:
        ( A ) ORGANISM: Mus musculus ( x i ) SEQUENCE DESCRIPTION: SEQ ID NO:10:

Trp  Ala  Ala  Glu  Glu  Lys  Lys  Trp  Val  Pro  Tyr  Arg  Val  Pro  Asn
    1                   5                        10                       15

( 2 ) INFORMATION FOR SEQ ID NO:11:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: Other
        ( A ) DESCRIPTION: OSF 5.1 (antigen peptide)
            segment of mouse OSF-5 from the 872nd to
            the 886th amino acid residue ( v i ) ORIGINAL SOURCE:
        ( A ) ORGANISM: Mus musculus ( x i ) SEQUENCE DESCRIPTION: SEQ ID NO:11:

Pro  His  Glu  Ser  Glu  Leu  Pro  Arg  Glu  Trp  Glu  Asn  Asn  Lys  Glu
    1                   5                        10                       15

( 2 ) INFORMATION FOR SEQ ID NO:12:

( i ) SEQUENCE CHARACTERISTICS:
        ( A ) LENGTH: 484 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Glu  Val  Val  Thr  Thr  Asp  Ser  Leu  Asp  Phe  Arg  His  His  Ser  Tyr  Lys
    1                   5                        10                       15

Asp  Met  Arg  Gln  Leu  Met  Lys  Ala  Val  Asn  Glu  Glu  Cys  Pro  Thr  Ile
                        20                       25                       30

Thr  Arg  Thr  Tyr  Ser  Leu  Gly  Lys  Ser  Ser  Arg  Gly  Leu  Lys  Ile  Tyr
                        35                       40                       45

Ala  Met  Glu  Ile  Ser  Asp  Asn  Pro  Gly  Asp  His  Glu  Leu  Gly  Glu  Pro

```
                  50                          55                          60
Glu  Phe  Arg  Tyr  Thr  Ala  Gly  Ile  His  Gly  Asn  Glu  Val  Leu  Gly  Arg
65                       70                       75                       80

Glu  Leu  Leu  Leu  Leu  Leu  Met  Gln  Tyr  Leu  Cys  Gln  Glu  Tyr  Arg  Asp
                    85                       90                       95

Gly  Asn  Pro  Arg  Val  Arg  Asn  Leu  Val  Gln  Asp  Thr  Arg  Ile  His  Leu
               100                      105                      110

Val  Pro  Ser  Leu  Asn  Pro  Asp  Gly  Tyr  Glu  Val  Ala  Ala  Gln  Met  Gly
          115                      120                      125

Ser  Glu  Phe  Gly  Asn  Trp  Ala  Leu  Gly  Leu  Trp  Thr  Glu  Glu  Gly  Phe
     130                      135                      140

Asp  Ile  Phe  Glu  Asp  Phe  Pro  Asp  Leu  Asn  Ser  Val  Leu  Trp  Ala  Ala
145                      150                      155                      160

Glu  Glu  Lys  Lys  Trp  Val  Pro  Tyr  Arg  Val  Pro  Asn  Asn  Asn  Leu  Pro
                    165                      170                      175

Ile  Pro  Glu  Arg  Tyr  Leu  Ser  Pro  Asp  Ala  Thr  Val  Ser  Thr  Glu  Val
               180                      185                      190

Arg  Ala  Ile  Ile  Ser  Trp  Met  Glu  Lys  Asn  Pro  Phe  Val  Leu  Gly  Ala
               195                      200                      205

Asn  Leu  Asn  Gly  Gly  Glu  Arg  Leu  Val  Ser  Tyr  Pro  Tyr  Asp  Met  Ala
     210                      215                      220

Arg  Thr  Pro  Ser  Gln  Glu  Gln  Leu  Leu  Ala  Glu  Ala  Leu  Ala  Ala  Ala
225                      230                      235                      240

Arg  Gly  Glu  Asp  Asp  Asp  Gly  Val  Ser  Glu  Ala  Gln  Glu  Thr  Pro  Asp
                    245                      250                      255

His  Ala  Ile  Phe  Arg  Trp  Leu  Ala  Ile  Ser  Phe  Ala  Ser  Ala  His  Leu
               260                      265                      270

Thr  Met  Thr  Glu  Pro  Tyr  Arg  Gly  Gly  Cys  Gln  Ala  Gln  Asp  Tyr  Thr
          275                      280                      285

Ser  Gly  Met  Gly  Ile  Val  Asn  Gly  Ala  Lys  Trp  Asn  Pro  Arg  Ser  Gly
     290                      295                      300

Thr  Phe  Asn  Asp  Phe  Ser  Tyr  Leu  His  Thr  Asn  Cys  Leu  Glu  Leu  Ser
305                      310                      315                      320

Val  Tyr  Leu  Gly  Cys  Asp  Lys  Phe  Pro  His  Glu  Ser  Glu  Leu  Pro  Arg
               325                      330                      335

Glu  Trp  Glu  Asn  Asn  Lys  Glu  Ala  Leu  Leu  Thr  Phe  Met  Glu  Gln  Val
               340                      345                      350

His  Arg  Gly  Ile  Lys  Gly  Val  Val  Thr  Asp  Glu  Gln  Gly  Ile  Pro  Ile
          355                      360                      365

Ala  Asn  Ala  Thr  Ile  Ser  Val  Ser  Gly  Ile  Asn  His  Gly  Val  Lys  Thr
     370                      375                      380

Ala  Ser  Gly  Gly  Asp  Tyr  Trp  Arg  Ile  Leu  Asn  Pro  Gly  Glu  Tyr  Arg
385                      390                      395                      400

Val  Thr  Ala  His  Ala  Glu  Gly  Tyr  Thr  Ser  Ser  Ala  Lys  Ile  Cys  Asn
               405                      410                      415

Val  Asp  Tyr  Asp  Ile  Gly  Ala  Thr  Gln  Cys  Asn  Phe  Ile  Leu  Ala  Arg
               420                      425                      430

Ser  Asn  Trp  Lys  Arg  Ile  Arg  Glu  Ile  Leu  Ala  Met  Asn  Gly  Asn  Arg
          435                      440                      445

Pro  Ile  Leu  Gly  Val  Asp  Pro  Ser  Arg  Pro  Met  Thr  Pro  Gln  Gln  Arg
     450                      455                      460

Arg  Met  Gln  Gln  Arg  Arg  Leu  Gln  Tyr  Arg  Leu  Arg  Met  Arg  Glu  Gln
465                      470                      475                      480
```

Met Gln Leu Arg (2) INFORMATION FOR SEQ ID NO:13:

(i) SEQUENCE CHARACTERISTICS:
        (A) LENGTH: 434 amino acids
        (B) TYPE: amino acid
        (D) TOPOLOGY: linear (ii) MOLECULE TYPE: peptide (xi) SEQUENCE DESCRIPTION: SEQ ID NO:13:

```
Arg Pro Gln Glu Asp Gly Ile Ser Phe Glu Tyr His Arg Tyr Pro Glu
 1               5                  10                  15

Leu Arg Glu Ala Leu Val Ser Val Trp Leu Gln Cys Ala Ala Val Ser
            20                  25                  30

Arg Ile Tyr Thr Val Gly Arg Ser Phe Glu Gly Arg Glu Leu Leu Val
        35                  40                  45

Leu Glu Leu Ser Asp Asn Pro Gly Val His Glu Pro Gly Glu Pro Glu
    50                  55                  60

Phe Lys Tyr Ile Gly Asn Met His Gly Asn Glu Ala Val Gly Arg Glu
65                  70                  75                  80

Leu Leu Ile Phe Leu Ala Gln Tyr Leu Cys Asn Glu Tyr Gln Lys Gly
                85                  90                  95

Asn Glu Thr Ile Val Gln Leu Ile His Asn Thr Arg Ile His Ile Met
            100                 105                 110

Pro Ser Leu Asn Pro Asp Gly Phe Glu Lys Ala Ala Ser Gln Leu Gly
        115                 120                 125

Glu Leu Lys Asp Trp Phe Val Gly Arg Ser Asn Ala Gln Gly Ile Asp
    130                 135                 140

Leu Asn Arg Asn Phe Pro Asp Leu Asp Arg Ile Val Tyr Ile Asn Glu
145                 150                 155                 160

Lys Glu Gly Gly Pro Asn Asn His Leu Leu Lys Asn Leu Lys Lys Ile
                165                 170                 175

Val Asp Gln Asn Thr Lys Leu Ala Pro Glu Thr Lys Ala Val Ile His
            180                 185                 190

Trp Ile Met Asp Ile Pro Phe Val Leu Ser Ala Asn Leu His Gly Gly
        195                 200                 205

Asp Leu Val Ala Asn Tyr Pro Tyr Asp Glu Thr Arg Ser Gly Ser Ala
    210                 215                 220

His Glu Tyr Ser Ser Cys Pro Asp Asp Asp Ile Phe Gln Ser Leu Ala
225                 230                 235                 240

Arg Ala Tyr Ser Ser Phe Asn Pro Pro Met Ser Asp Pro Asp Arg Pro
                245                 250                 255

Pro Cys Arg Lys Asn Asp Asp Asp Ser Ser Phe Val Glu Gly Thr Thr
            260                 265                 270

Asn Gly Ala Ala Trp Tyr Ser Val Pro Gly Gly Met Gln Asp Phe Asn
        275                 280                 285

Tyr Leu Ser Ser Asn Cys Phe Glu Ile Thr Val Glu Leu Ser Cys Glu
    290                 295                 300

Lys Phe Pro Pro Glu Glu Thr Leu Lys Asn Tyr Trp Glu Asp Asn Lys
305                 310                 315                 320

Asn Ser Leu Ile Ser Tyr Ile Gln Gln Ile His Arg Gly Val Lys Gly
                325                 330                 335

Phe Val Arg Asp Leu Gln Gly Asn Pro Ile Ala Asn Ala Thr Leu Ser
```

-continued

```
                          340                         345                          350
        Val Glu Gly Ile Asp His Asp Val Thr Ser Ala Lys Asp Gly Asp Tyr
                    355                         360                    365

Trp Arg Leu Leu Val Pro Gly Asn Tyr Lys Leu Thr Ala Ser Ala Pro
                    370                         375                    380

Gly Tyr Leu Ala Ile Ala Lys Lys Val Ala Val Pro Tyr Ser Pro Ala
        385                         390                    395                    400

Val Arg Val Asp Phe Glu Leu Glu Ser Phe Ser Glu Arg Lys Glu Glu
                            405                    410                    415

Glu Lys Glu Glu Leu Met Glu Trp Trp Lys Met Met Ser Glu Thr Leu
                    420                         425                    430

Asn Phe
```

( 2 ) INFORMATION FOR SEQ ID NO:14:

( i ) SEQUENCE CHARACTERISTICS:
        ( A ) LENGTH: 435 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
        Arg Leu Gln Gln Glu Asp Gly Ile Ser Phe Glu Tyr His Arg Tyr Pro
        1               5                       10                      15

Glu Leu Arg Glu Ala Leu Val Ser Val Trp Leu Gln Cys Thr Ala Ile
                    20                      25                      30

Ser Arg Ile Tyr Thr Val Gly Arg Ser Phe Glu Gly Arg Glu Leu Leu
                    35                      40                      45

Val Ile Glu Leu Ser Asp Asn Pro Gly Val His Glu Pro Gly Glu Pro
                50                      55                      60

Glu Phe Lys Tyr Ile Gly Asn Met His Gly Asn Glu Ala Val Gly Arg
        65                      70                      75                      80

Glu Leu Leu Ile Phe Leu Ala Gln Tyr Leu Cys Asn Glu Tyr Gln Arg
                            85                      90                      95

Gly Asn Glu Thr Ile Val Asn Leu Ile His Ser Thr Arg Ile His Ile
                        100                     105                     110

Met Pro Ser Leu Asn Pro Asp Gly Phe Glu Lys Ala Ala Ser Gln Pro
                    115                     120                     125

Gly Glu Leu Lys Asp Trp Phe Val Gly Arg Ser Asn Ala Gln Gly Ile
                130                     135                     140

Asp Leu Asn Arg Asn Phe Pro Asp Leu Asp Arg Ile Val Tyr Val Asn
        145                     150                     155                     160

Glu Lys Glu Gly Gly Pro Asn Asn His Leu Leu Lys Asn Leu Lys Lys
                            165                     170                     175

Ile Val Asp Gln Asn Ser Lys Leu Ala Pro Glu Thr Lys Ala Val Ile
                        180                     185                     190

His Trp Ile Met Asp Ile Pro Phe Val Leu Ser Ala Asn Leu His Gly
                    195                     200                     205

Gly Asp Leu Val Ala Asn Tyr Pro Tyr Asp Glu Thr Arg Ser Gly Thr
                210                     215                     220

Ala His Glu Tyr Ser Ser Cys Pro Asp Asp Ala Ile Phe Gln Ser Leu
        225                     230                     235                     240

Ala Arg Ala Tyr Ser Ser Phe Asn Pro Val Met Ser Asp Pro Asn Arg
                            245                     250                     255
```

```
Pro  Pro  Cys  Arg  Lys  Asn  Asp  Asp  Asp  Ser  Ser  Phe  Val  Asp  Gly  Thr
          260                 265                      270

Thr  Asn  Gly  Gly  Ala  Trp  Tyr  Ser  Val  Pro  Gly  Gly  Met  Gln  Asp  Phe
          275                 280                      285

Asn  Tyr  Leu  Ser  Ser  Asn  Cys  Phe  Glu  Ile  Thr  Val  Glu  Leu  Ser  Cys
          290                 295                      300

Glu  Lys  Phe  Pro  Pro  Glu  Glu  Thr  Leu  Lys  Ser  Tyr  Trp  Glu  Asp  Asn
305                      310                 315                           320

Lys  Asn  Ser  Leu  Ile  Asn  Tyr  Leu  Glu  Gln  Ile  His  Arg  Gly  Val  Lys
               325                      330                           335

Gly  Phe  Val  Arg  Asp  Leu  Gln  Gly  Asn  Pro  Ile  Ala  Asn  Ala  Thr  Ile
               340                 345                      350

Ser  Val  Asp  Gly  Ile  Asp  His  Asp  Val  Thr  Ser  Ala  Lys  Asp  Gly  Asp
               355                 360                      365

Tyr  Trp  Arg  Leu  Leu  Val  Pro  Gly  Asn  Tyr  Lys  Leu  Thr  Ala  Ser  Ala
          370                 375                      380

Pro  Gly  Tyr  Leu  Ala  Ile  Thr  Lys  Lys  Val  Ala  Val  Pro  Phe  Ser  Pro
385                      390                 395                           400

Ala  Val  Gly  Val  Asp  Phe  Glu  Leu  Glu  Ser  Phe  Ser  Glu  Arg  Lys  Glu
               405                 410                      415

Glu  Glu  Lys  Glu  Glu  Leu  Met  Glu  Trp  Trp  Lys  Met  Met  Ser  Glu  Thr
               420                 425                      430

Leu  Asn  Phe
          435
```

(2) INFORMATION FOR SEQ ID NO:15:

(i) SEQUENCE CHARACTERISTICS:
        (A) LENGTH: 435 amino acids
        (B) TYPE: amino acid
        (D) TOPOLOGY: linear (ii) MOLECULE TYPE: peptide (xi) SEQUENCE DESCRIPTION: SEQ ID NO:15:

```
Arg  Leu  Gln  Gln  Glu  Asp  Gly  Ile  Ser  Phe  Glu  Tyr  His  Arg  Tyr  Pro
1                   5                   10                      15

Glu  Leu  Arg  Glu  Ala  Leu  Val  Ser  Val  Trp  Leu  Gln  Cys  Thr  Ala  Ile
               20                  25                      30

Ser  Arg  Ile  Tyr  Thr  Val  Gly  Arg  Thr  Phe  Glu  Gly  Arg  Glu  Leu  Leu
          35                  40                      45

Val  Ile  Glu  Leu  Ser  Asp  Asn  Pro  Gly  Val  His  Glu  Pro  Gly  Glu  Pro
     50                  55                      60

Glu  Phe  Lys  Tyr  Ile  Gly  Asn  Met  His  Gly  Asn  Glu  Ala  Val  Gly  Arg
65                       70                  75                           80

Glu  Leu  Leu  Ile  Phe  Leu  Ala  Gln  Tyr  Leu  Cys  Asn  Glu  Tyr  Gln  Arg
               85                  90                      95

Gly  Asn  Glu  Thr  Ile  Val  Asn  Leu  Ile  His  Ser  Thr  Arg  Ile  His  Ile
               100                 105                     110

Met  Pro  Ser  Leu  Asn  Pro  Asp  Gly  Phe  Glu  Lys  Ala  Ala  Ser  Gln  Pro
               115                 120                     125

Gly  Glu  Leu  Lys  Asp  Trp  Phe  Val  Gly  Arg  Ser  Asn  Ala  Gln  Gly  Ile
          130                 135                     140

Asp  Leu  Asn  Arg  Asn  Phe  Pro  Asp  Leu  Asp  Arg  Ile  Val  Tyr  Val  Asn
145                      150                 155                          160

Glu  Lys  Glu  Gly  Gly  Pro  Asn  Asn  His  Leu  Leu  Lys  Asn  Leu  Lys  Lys
```

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |
| Ile | Val | Asp | Gln<br>180 | Asn | Ser | Lys | Leu | Ala<br>185 | Pro | Glu | Thr | Lys<br>190 | Ala | Val | Ile |
| His | Trp | Ile<br>195 | Met | Asp | Ile | Pro | Phe<br>200 | Val | Leu | Ser | Ala | Asn<br>205 | Leu | His | Gly |
| Gly | Asp<br>210 | Leu | Val | Ala | Asn | Tyr<br>215 | Pro | Tyr | Asp | Glu | Thr<br>220 | Arg | Ser | Gly | Thr |
| Ala<br>225 | His | Glu | Tyr | Ser | Ser<br>230 | Cys | Pro | Asp | Asp | Ala<br>235 | Ile | Phe | Gln | Ser | Leu<br>240 |
| Ala | Arg | Ala | Tyr | Ser<br>245 | Ser | Phe | Asn | Pro | Val<br>250 | Met | Ser | Asp | Pro | Asn<br>255 | Arg |
| Pro | Pro | Cys | Arg<br>260 | Lys | Asn | Asp | Asp | Ser<br>265 | Ser | Phe | Val | Asp<br>270 | Gly | Thr |
| Thr | Asn | Gly<br>275 | Gly | Ala | Trp | Tyr | Ser<br>280 | Val | Pro | Gly | Gly | Met<br>285 | Gln | Asp | Phe |
| Asn | Tyr<br>290 | Leu | Ser | Ser | Asn | Cys<br>295 | Phe | Glu | Ile | Thr | Val<br>300 | Glu | Leu | Ser | Cys |
| Glu<br>305 | Lys | Phe | Pro | Pro | Glu<br>310 | Glu | Thr | Leu | Lys | Ser<br>315 | Tyr | Trp | Glu | Asp | Asn<br>320 |
| Lys | Asn | Ser | Leu | Ile<br>325 | Asn | Tyr | Leu | Glu | Gln<br>330 | Ile | His | Arg | Gly | Val<br>335 | Lys |
| Gly | Phe | Val | Arg<br>340 | Asp | Leu | Gln | Gly | Asn<br>345 | Pro | Ile | Ala | Asn<br>350 | Ala | Thr | Ile |
| Ser | Val | Asp<br>355 | Gly | Ile | Asp | His<br>360 | Asp | Val | Thr | Ser | Ala<br>365 | Lys | Asp | Gly | Asp |
| Tyr | Trp<br>370 | Arg | Leu | Leu | Val<br>375 | Pro | Gly | Asn | Tyr | Lys<br>380 | Leu | Thr | Ala | Ser | Ala |
| Pro<br>385 | Gly | Tyr | Leu | Ala | Ile<br>390 | Thr | Lys | Lys | Val | Ala<br>395 | Val | Pro | Phe | Ser | Pro<br>400 |
| Ala | Val | Gly | Val | Asp<br>405 | Phe | Glu | Leu | Glu | Ser<br>410 | Phe | Ser | Glu | Arg | Lys<br>415 | Glu |
| Glu | Glu | Lys | Glu<br>420 | Glu | Leu | Met | Glu | Trp<br>425 | Trp | Lys | Met | Met | Ser<br>430 | Glu | Thr |
| Leu | Asn | Phe<br>435 |

( 2 ) INFORMATION FOR SEQ ID NO:16:

( i ) SEQUENCE CHARACTERISTICS:
        ( A ) LENGTH: 435 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

| Arg<br>1 | Leu | Gln | Gln | Glu<br>5 | Asp | Gly | Ile | Ser | Phe<br>10 | Glu | Tyr | His | Arg | Tyr<br>15 | Pro |
| --- | --- | --- | --- | --- | --- | --- | --- | --- | --- | --- | --- | --- | --- | --- | --- |
| Glu | Leu | Arg | Glu<br>20 | Ala | Leu | Val | Ser | Val<br>25 | Trp | Leu | Gln | Cys | Thr<br>30 | Ala | Ile |
| Ser | Arg | Ile<br>35 | Tyr | Thr | Val | Gly | Arg<br>40 | Ser | Phe | Glu | Gly | Arg<br>45 | Glu | Leu | Leu |
| Val | Ile<br>50 | Glu | Leu | Ser | Asp | Asn<br>55 | Pro | Gly | Val | His | Glu<br>60 | Pro | Gly | Glu | Pro |
| Glu<br>65 | Phe | Lys | Tyr | Ile | Gly<br>70 | Asn | Met | His | Gly | Asn<br>75 | Glu | Ala | Val | Gly | Arg<br>80 |

|     |     |     |     |     |     |     |     |     |     |     |     |     |     |     |
|-----|-----|-----|-----|-----|-----|-----|-----|-----|-----|-----|-----|-----|-----|-----|
| Glu | Leu | Leu | Ile | Phe<br>85 | Leu | Ala | Gln | Tyr | Leu<br>90 | Cys | Asn | Glu | Tyr | Gln<br>95 | Lys |
| Gly | Asn | Glu | Thr<br>100 | Ile | Val | Asn | Leu | Ile<br>105 | His | Ser | Thr | Arg<br>110 | Ile | His | Ile |
| Met | Pro | Ser<br>115 | Leu | Asn | Pro | Asp | Gly<br>120 | Phe | Glu | Lys | Ala | Ala<br>125 | Ser | Gln | Pro |
| Gly | Glu<br>130 | Leu | Lys | Asp | Trp | Phe<br>135 | Val | Gly | Arg | Ser | Asn<br>140 | Ala | Gln | Gly | Ile |
| Asp<br>145 | Leu | Asn | Arg | Asn | Phe<br>150 | Pro | Asp | Leu | Asp | Arg<br>155 | Ile | Val | Tyr | Val | Asn<br>160 |
| Glu | Lys | Glu | Gly | Gly<br>165 | Pro | Asn | Asn | His | Leu<br>170 | Leu | Lys | Asn | Met | Lys<br>175 | Lys |
| Ile | Val | Asp | Gln<br>180 | Asn | Thr | Lys | Leu | Ala<br>185 | Pro | Glu | Thr | Lys<br>190 | Ala | Val | Ile |
| His | Trp | Ile<br>195 | Met | Asp | Ile | Pro<br>200 | Phe | Val | Leu | Ser | Ala<br>205 | Asn | Leu | His | Gly |
| Gly | Asp<br>210 | Leu | Val | Ala | Asn | Tyr<br>215 | Pro | Tyr | Asp | Glu | Thr<br>220 | Arg | Ser | Gly | Ser |
| Ala<br>225 | His | Glu | Tyr | Ser | Ser<br>230 | Ser | Pro | Asp | Asp | Ala<br>235 | Ile | Phe | Gln | Ser | Leu<br>240 |
| Ala | Arg | Ala | Tyr | Ser<br>245 | Ser | Phe | Asn | Pro | Ala<br>250 | Met | Ser | Asp | Pro | Asn<br>255 | Arg |
| Pro | Pro | Cys<br>260 | Arg | Lys | Asn | Asp | Asp<br>265 | Ser | Ser | Phe | Val | Asp<br>270 | Gly | Thr |
| Thr | Asn | Gly<br>275 | Gly | Ala | Trp | Tyr | Ser<br>280 | Val | Pro | Gly | Gly | Met<br>285 | Gln | Asp | Phe |
| Asn | Tyr<br>290 | Leu | Ser | Ser | Asn | Cys<br>295 | Phe | Glu | Ile | Thr | Val<br>300 | Glu | Leu | Ser | Cys |
| Glu<br>305 | Lys | Phe | Pro | Pro | Glu<br>310 | Glu | Thr | Leu | Lys | Thr<br>315 | Tyr | Trp | Glu | Asp | Asn<br>320 |
| Lys | Asn | Ser | Leu | Ile<br>325 | Ser | Tyr | Leu | Glu | Gln<br>330 | Ile | His | Arg | Gly | Val<br>335 | Lys |
| Gly | Phe | Val | Arg<br>340 | Asp | Leu | Gln | Gly | Asn<br>345 | Pro | Ile | Ala | Asn<br>350 | Ala | Thr | Ile |
| Ser | Val | Glu<br>355 | Gly | Ile | Asp | His | Asp<br>360 | Val | Thr | Ser | Ala | Lys<br>365 | Asp | Gly | Asp |
| Tyr | Trp<br>370 | Arg | Leu | Leu | Ile | Pro<br>375 | Gly | Asn | Tyr | Lys | Leu<br>380 | Thr | Ala | Ser | Ala |
| Pro<br>385 | Gly | Tyr | Leu | Ala | Ile<br>390 | Thr | Lys | Lys | Val | Ala<br>395 | Val | Pro | Tyr | Ser | Pro<br>400 |
| Ala | Ala | Gly | Val | Asp<br>405 | Phe | Glu | Leu | Glu | Ser<br>410 | Phe | Ser | Glu | Arg | Lys<br>415 | Glu |
| Glu | Glu | Lys | Glu<br>420 | Glu | Leu | Met | Glu | Trp<br>425 | Trp | Lys | Met | Met | Ser<br>430 | Glu | Thr |
| Leu | Asn | Phe<br>435 |     |     |     |     |     |     |     |     |     |     |     |     |     |

( 2 ) INFORMATION FOR SEQ ID NO:17:

( i ) SEQUENCE CHARACTERISTICS:
   ( A ) LENGTH: 438 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:17:

```
Val Thr Phe Arg His His Arg Tyr Asp Asp Leu Val Arg Thr Leu Tyr
 1               5                  10                  15

Lys Val Gln Asn Glu Cys Pro Gly Ile Thr Arg Val Tyr Ser Ile Gly
             20                  25                  30

Arg Ser Val Glu Gly Arg His Leu Tyr Val Leu Glu Phe Ser Asp His
             35                  40                  45

Pro Gly Ile His Glu Pro Leu Glu Pro Glu Val Lys Tyr Val Gly Asn
         50                  55                  60

Met His Gly Asn Glu Ala Leu Gly Arg Glu Leu Met Leu Gln Leu Ser
 65                  70                  75                  80

Glu Phe Leu Cys Glu Glu Phe Arg Asn Arg Asn Gln Arg Ile Val Gln
                 85                  90                  95

Leu Ile Gln Asp Thr Arg Ile His Ile Leu Pro Ser Met Asn Pro Asp
                100                 105                 110

Gly Tyr Glu Val Ala Ala Ala Gln Gly Pro Asn Lys Pro Gly Tyr Leu
            115                 120                 125

Val Gly Arg Asn Asn Ala Asn Gly Val Asp Leu Asn Arg Asn Phe Pro
130                 135                 140

Asp Leu Asn Thr Tyr Ile Tyr Tyr Asn Glu Lys Tyr Gly Gly Pro Asn
145                 150                 155                 160

His His Leu Pro Leu Pro Asp Asn Trp Lys Ser Gln Val Glu Pro Glu
                165                 170                 175

Thr Arg Ala Val Ile Arg Trp Met His Ser Phe Asn Phe Val Leu Ser
            180                 185                 190

Ala Asn Leu His Gly Gly Ala Val Val Ala Asn Tyr Pro Tyr Asp Lys
            195                 200                 205

Ser Phe Glu His Arg Val Arg Gly Val Arg Arg Thr Ala Ser Thr Pro
    210                 215                 220

Thr Pro Asp Asp Lys Leu Phe Gln Lys Leu Ala Lys Val Tyr Ser Tyr
225                 230                 235                 240

Ala His Gly Trp Met Phe Gln Gly Trp Asn Cys Gly Asp Tyr Phe Pro
                245                 250                 255

Asp Gly Ile Thr Asn Gly Ala Ser Trp Tyr Ser Leu Ser Lys Gly Met
            260                 265                 270

Gln Asp Phe Asn Tyr Leu His Thr Asn Cys Phe Glu Ile Thr Leu Glu
    275                 280                 285

Leu Ser Cys Asp Lys Phe Pro Pro Glu Glu Glu Leu Gln Arg Glu Trp
    290                 295                 300

Leu Gly Asn Arg Glu Ala Leu Ile Gln Phe Leu Glu Gln Val His Gln
305                 310                 315                 320

Gly Ile Lys Gly Met Val Leu Asp Glu Asn Tyr Asn Asn Leu Ala Asn
            325                 330                 335

Ala Val Ile Ser Val Ser Gly Ile Asn His Asp Val Thr Ser Gly Asp
            340                 345                 350

His Gly Asp Tyr Phe Arg Leu Leu Leu Pro Gly Ile Tyr Thr Val Ser
    355                 360                 365

Ala Thr Ala Pro Gly Tyr Asp Pro Glu Thr Val Thr Val Thr Val Gly
370                 375                 380

Pro Ala Glu Pro Thr Leu Val Asn Phe His Leu Lys Arg Ser Ile Pro
385                 390                 395                 400

Gln Val Ser Pro Val Arg Arg Ala Pro Ser Arg Arg His Gly Val Arg
```

```
                        405                          410                          415
Ala  Lys  Val  Gln  Pro  Gln  Ala  Arg  Lys  Lys  Glu  Met  Glu  Met  Arg  Gln
               420                          425                          430

Leu  Gln  Arg  Gly  Pro  Ala
               435
```

(2) INFORMATION FOR SEQ ID NO:18:

(i) SEQUENCE CHARACTERISTICS:
       (A) LENGTH: 132 amino acids
       (B) TYPE: amino acid
       (D) TOPOLOGY: linear (ii) MOLECULE TYPE: peptide (xi) SEQUENCE DESCRIPTION: SEQ ID NO:18:

```
Phe  His  Tyr  Val  Cys  Arg  Tyr  Gly  Gly  Glu  Ser  Asp  Pro  Gly  His  Glu
1                   5                        10                          15

Glu  Pro  Glu  Tyr  His  Gly  Asn  Glu  Gly  Arg  Glu  Leu  Leu  Leu  Cys  Glu
               20                          25                          30

Asn  Leu  Thr  Arg  Ile  His  Pro  Ser  Asn  Pro  Asp  Gly  Glu  Ala  Ala  Gly
               35                          40                          45

Gly  Asp  Phe  Pro  Asp  Leu  Glu  Pro  Asn  Leu  Glu  Ala  Ile  Trp  Phe  Val
          50                          55                          60

Leu  Ala  Asn  Leu  Gly  Gly  Tyr  Pro  Tyr  Asp  Pro  Asp  Phe  Leu  Ala  Met
65                            70                          75                     80

Gly  Asn  Gly  Trp  Asp  Phe  Tyr  Leu  Asn  Cys  Glu  Leu  Cys  Lys  Phe  Pro
                    85                          90                          95

Glu  Leu  Trp  Asn  Leu  Gln  His  Gly  Lys  Gly  Val  Asp  Ala  Asn  Ala  Ser
               100                         105                         110

Val  Gly  Ile  His  Val  Gly  Asp  Tyr  Arg  Leu  Pro  Gly  Tyr  Ala  Ala  Gly
               115                         120                         125

Tyr  Val  Phe  Leu
               130
```

(2) INFORMATION FOR SEQ ID NO:19:

(i) SEQUENCE CHARACTERISTICS:
       (A) LENGTH: 109 amino acids
       (B) TYPE: amino acid
       (D) TOPOLOGY: linear (ii) MOLECULE TYPE: peptide (xi) SEQUENCE DESCRIPTION: SEQ ID NO:19:

```
Ala  Trp  Cys  Ala  Glu  Asp  Glu  Ser  Gln  Thr  Gln  Trp  Ile  Glu  Val  Asp
1                   5                        10                          15

Thr  Arg  Arg  Thr  Thr  Arg  Phe  Thr  Gly  Val  Ile  Thr  Gln  Gly  Arg  Asp
               20                          25                          30

Ser  Ser  Ile  His  Asp  Asp  Phe  Val  Thr  Thr  Phe  Phe  Val  Gly  Phe  Ser
               35                          40                          45

Asn  Asp  Ser  Gln  Thr  Trp  Val  Met  Tyr  Thr  Asn  Gly  Tyr  Glu  Glu  Met
          50                          55                          60

Thr  Phe  Tyr  Gly  Asn  Val  Asp  Lys  Asp  Thr  Pro  Val  Leu  Ser  Glu  Leu
65                            70                          75                     80

Pro  Glu  Pro  Val  Val  Ala  Arg  Phe  Ile  Arg  Ile  Tyr  Pro  Leu  Thr  Trp
                    85                          90                          95

Asn  Gly  Ser  Leu  Cys  Met  Arg  Leu  Glu  Val  Leu  Gly  Cys
               100                         105
```

( 2 ) INFORMATION FOR SEQ ID NO:20:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Ala Trp Ser Thr Lys Glu Pro Phe Ser Trp Ile Lys Val Asp Leu Leu
 1               5                  10                  15

Ala Pro Met Ile Ile His Gly Ile Lys Thr Gln Gly Ala Arg Gln Lys
                 20              25                  30

Phe Ser Ser Leu Tyr Ile Ser Gln Phe Ile Ile Met Tyr Ser Leu Asp
             35              40                  45

Gly Lys Lys Trp Gln Thr Tyr Arg Gly Asn Ser Thr Gly Thr Leu Met
     50              55                  60

Val Phe Phe Gly Asn Val Asp Ser Ser Gly Ile Lys His Asn Ile Phe
65                   70                  75                  80

Asn Pro Pro Ile Ile Ala Arg Tyr Ile Arg Leu His Pro Thr His Tyr
                 85              90                  95

Ser Ile Arg Ser Thr Leu Arg Met Glu Leu Met Gly Cys
                100             105
```

( 2 ) INFORMATION FOR SEQ ID NO:21:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Ala Trp Arg Pro Gln Val Asn Asn Pro Lys Glu Trp Leu Gln Val Asp
 1               5                  10                  15

Phe Gln Lys Thr Met Lys Val Thr Gly Val Thr Thr Gln Gly Val Lys
                 20              25                  30

Ser Leu Leu Thr Ser Met Tyr Val Lys Glu Phe Leu Ile Ser Ser Ser
             35              40                  45

Gln Asp Gly His Gln Trp Thr Leu Phe Phe Gln Asn Gly Lys Val Lys
     50              55                  60

Val Phe Gln Gly Asn Gln Asp Ser Phe Thr Pro Val Val Asn Ser Leu
65                   70                  75                  80

Asp Pro Pro Leu Leu Thr Arg Tyr Leu Arg Ile His Pro Gln Ser Trp
                 85              90                  95

Val His Gln Ile Ala Leu Arg Met Glu Val Leu Gly Cys
                100             105
```

( 2 ) INFORMATION FOR SEQ ID NO:22:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Ala  Trp  Ser  Val  Glu  Lys  Leu  Ala  Ala  Glu  Phe  Ala  Ser  Lys  Pro  Trp
1              5                        10                       15

Ile  Gln  Val  Asp  Met  Gln  Lys  Glu  Val  Ile  Ile  Thr  Gly  Ile  Gln  Thr
               20                       25                       30

Gln  Gly  Ala  Lys  His  Tyr  Leu  Lys  Ser  Cys  Tyr  Thr  Thr  Glu  Phe  Tyr
          35                       40                       45

Val  Ala  Tyr  Ser  Ser  Asn  Gln  Ile  Asn  Trp  Gln  Ile  Phe  Lys  Gly  Asn
     50                       55                       60

Ser  Thr  Arg  Asn  Val  Met  Tyr  Phe  Asn  Gly  Asn  Ser  Asp  Ala  Ser  Thr
65                       70                       75                       80

Ile  Lys  Glu  Asn  Gln  Phe  Asp  Pro  Pro  Ile  Val  Ala  Arg  Tyr  Ile  Arg
               85                       90                       95

Ile  Ser  Pro  Thr  Arg  Ala  Tyr  Asn  Arg  Pro  Thr  Leu  Arg  Leu  Glu  Leu
               100                      105                      110

Gln  Gly  Cys
          115
```

( 2 ) INFORMATION FOR SEQ ID NO:23:

( i ) SEQUENCE CHARACTERISTICS:
      ( A ) LENGTH: 111 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:23:

```
Ala  Trp  Gln  Ala  Lys  Ala  Asn  Asn  Asn  Lys  Gln  Trp  Leu  Glu  Ile  Asp
1              5                        10                       15

Leu  Leu  Lys  Ile  Lys  Lys  Ile  Thr  Ala  Ile  Ile  Thr  Gln  Gly  Cys  Lys
               20                       25                       30

Ser  Leu  Ser  Ser  Glu  Met  Tyr  Val  Lys  Ser  Tyr  Thr  Ile  His  Tyr  Ser
          35                       40                       45

Glu  Gln  Gly  Val  Glu  Trp  Lys  Pro  Tyr  Arg  Leu  Lys  Ser  Ser  Met  Val
     50                       55                       60

Asp  Lys  Ile  Phe  Glu  Gly  Asn  Thr  Asn  Thr  Lys  Gly  His  Val  Lys  Asn
65                       70                       75                       80

Phe  Phe  Asn  Pro  Pro  Ile  Ile  Ser  Arg  Phe  Ile  Arg  Val  Ile  Pro  Lys
               85                       90                       95

Thr  Trp  Asn  Gln  Ser  Ile  Thr  Leu  Arg  Leu  Glu  Leu  Phe  Gly  Cys
               100                      105                      110
```

( 2 ) INFORMATION FOR SEQ ID NO:24:

( i ) SEQUENCE CHARACTERISTICS:
      ( A ) LENGTH: 110 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:24:

```
Ala  Trp  His  Ala  Ser  Asn  Tyr  Asp  Ser  Lys  Pro  Trp  Ile  Gln  Val  Asn
1              5                        10                       15

Leu  Leu  Arg  Lys  Met  Arg  Val  Ser  Gly  Val  Met  Thr  Gln  Gly  Ala  Ser
               20                       25                       30

Arg  Ala  Gly  Arg  Ala  Glu  Tyr  Leu  Lys  Thr  Phe  Lys  Val  Ala  Tyr  Ser
          35                       40                       45

Leu  Asp  Gly  Arg  Lys  Phe  Glu  Phe  Ile  Gln  Asp  Glu  Ser  Gly  Gly  Asp
```

```
          50                   55                          60
    Lys  Glu  Phe  Leu  Gly  Asn  Leu  Asp  Asn  Asn  Ser  Leu  Lys  Val  Asn  Met
    65                        70                       75                         80

Phe  Asn  Pro  Thr  Leu  Glu  Ala  Gln  Tyr  Ile  Arg  Leu  Tyr  Pro  Val  Ser
                        85                  90                       95

Cys  His  Arg  Gly  Cys  Thr  Leu  Arg  Phe  Glu  Leu  Leu  Gly  Cys
                        100                 105                      110
```

( 2 ) INFORMATION FOR SEQ ID NO:25:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
    Ala  Trp  Thr  Ala  Gln  Ser  Asn  Ser  Ala  Lys  Glu  Trp  Leu  Gln  Val  Asp
    1                    5                       10                         15

Leu  Gly  Thr  Gln  Arg  Gln  Val  Thr  Gly  Ile  Ile  Thr  Gln  Gly  Ala  Arg
                        20                  25                       30

Asp  Phe  Gly  His  Ile  Gln  Tyr  Val  Glu  Ser  Tyr  Lys  Val  Ala  His  Ser
                        35                  40                       45

Asp  Asp  Gly  Val  Gln  Trp  Thr  Val  Tyr  Glu  Glu  Gln  Gly  Ser  Ser  Lys
                   50                  55                       60

Val  Phe  Gln  Gly  Asn  Leu  Asp  Asn  Asn  Ser  His  Lys  Lys  Asn  Ile  Phe
    65                        70                       75                         80

Glu  Lys  Pro  Phe  Met  Ala  Arg  Tyr  Val  Arg  Val  Leu  Pro  Val  Ser  Trp
                        85                  90                       95

His  Asn  Arg  Ile  Thr  Leu  Arg  Leu  Glu  Leu  Leu  Gly  Cys
                        100                 105
```

( 2 ) INFORMATION FOR SEQ ID NO:26:

( i ) SEQUENCE CHARACTERISTICS:
        ( A ) LENGTH: 104 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
    Ala  Trp  Cys  Ser  Ser  Ile  Val  Asp  Thr  Asn  Gln  Tyr  Ile  Val  Ala  Gly
    1                    5                       10                         15

Cys  Glu  Val  Pro  Arg  Thr  Phe  Met  Cys  Val  Ala  Leu  Gln  Gly  Arg  Gly
                        20                  25                       30

Asp  His  Asp  Gln  Trp  Val  Thr  Ser  Tyr  Lys  Ile  Arg  Tyr  Ser  Leu  Asp
                        35                  40                       45

Asn  Val  Thr  Trp  Ser  Glu  Tyr  Arg  Asn  Gly  Ala  Ala  Ile  Thr  Gly  Val
                   50                  55                       60

Thr  Asp  Arg  Asn  Thr  Val  Val  Asn  His  Phe  Phe  Asp  Thr  Pro  Ile  Arg
    65                        70                       75                         80

Ala  Arg  Ser  Ile  Ala  Ile  His  Pro  Leu  Thr  Trp  Asn  Asn  His  Ile  Ser
                        85                  90                       95

Leu  Arg  Cys  Glu  Phe  Tyr  Thr  Gln
                        100
```

( 2 ) INFORMATION FOR SEQ ID NO:27:

( i ) SEQUENCE CHARACTERISTICS:
    ( A ) LENGTH: 41 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:27:

```
Ala  Trp  Trp  Val  Asp  Leu  Gly  Thr  Gln  Gly  Tyr  Val  Phe  Tyr  Ser  Asp
 1                  5                        10                       15
Trp  Tyr  Phe  Gly  Asn  Asp  Asn  Phe  Pro  Ala  Arg  Tyr  Ile  Arg  Ile  Pro
               20                  25                       30
Trp  Leu  Arg  Leu  Glu  Leu  Leu  Gly  Cys
          35                  40
```

\* \* \* \* \*